US006554872B2

(12) United States Patent
Genet et al.

(10) Patent No.: US 6,554,872 B2
(45) Date of Patent: *Apr. 29, 2003

(54) CATIONIC AMINODIANTHRAQUINONES, USE, DYEING COMPOSITIONS CONTAINING THEM AND METHODS OF DYEING

(76) Inventors: Alain Genet, 9, Rue des Coquelicots, 93600 Aulnay Sous Bois (FR); Alain Lagrange, 5, Rue de Montry, 77700 Coupvray (FR)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/450,218

(22) Filed: Nov. 29, 1999

(65) Prior Publication Data

US 2001/0049848 A1 Dec. 13, 2001

(30) Foreign Application Priority Data

Nov. 30, 1998 (FR) .............................. 98 15045

(51) Int. Cl.⁷ .................................................. A61K 7/18
(52) U.S. Cl. .................................. 8/426; 8/405
(58) Field of Search ..................... 8/405, 426

(56) References Cited

U.S. PATENT DOCUMENTS

| 5,169,403 A | 12/1992 | Chan et al. ............ 8/405 |
| 5,314,505 A | 5/1994 | Chan et al. ............ 8/426 |
| 5,486,629 A | 1/1996 | Chan et al. ............ 552/236 |
| 5,520,707 A | 5/1996 | Lim et al. ............ 8/426 |

FOREIGN PATENT DOCUMENTS

| DE | 2 338 151 | 2/1974 |
| EP | 0 818 193 | 1/1998 |
| EP | 0 852 136 | 7/1998 |
| FR | 1 379 649 | 10/1964 |
| FR | 1 391 675 | 2/1965 |
| FR | 1 401 163 | 4/1965 |
| FR | 1 422 016 | 11/1965 |
| FR | 1 430 089 | 1/1966 |
| FR | 1 584 965 | 12/1969 |
| FR | 2 050 397 | 4/1971 |
| FR | 2 548 895 | 1/1985 |
| GB | 2 088 417 | 6/1982 |

OTHER PUBLICATIONS

English language Derwent Abstract of DE 2 338 151, Feb. 1974.
English language abstract of EP 0 852 136, Jul. 1998.
English language Derwent Abstract of FR 1 584 965, Dec. 1969.
English language Derwent Abstract of FR 2 050 397, Apr. 1971.
English language Derwent Abstract of FR 2 548 895, Jan. 1985.

*Primary Examiner*—Margaret Einsmann
(74) *Attorney, Agent, or Firm*—Finnegan, Henderson, Farabow, Garrett and Dunner LLP

(57) ABSTRACT

The invention relates to cationic aminodianthraquinones containing at least one cationic group Z, Z being chosen from quaternized aliphatic chains, aliphatic chains containing at least one quaternized saturated ring and aliphatic chains containing at least one quaternized unsaturated ring, their use as direct dye in compositions for dyeing keratinous materials, in particular human keratinous fibers such as hair, the dyeing compositions containing them, as well as the dyeing methods using them.

10 Claims, No Drawings

CATIONIC AMINODIANTHRAQUINONES, USE, DYEING COMPOSITIONS CONTAINING THEM AND METHODS OF DYEING

The present invention relates to cationic aminodianthraquinones containing at least one cationic group Z, with Z being chosen from quaternized aliphatic chains, aliphatic chains containing at least one quaternized saturated ring, and aliphatic chains containing at least one quaternized unsaturated ring, their use as direct dyes in applications for dyeing keratinous materials, such as human keratinous fibers, for example hair, the dyeing compositions containing them, as well as the dyeing methods using them.

It is known to dye keratinous fibers, and in particular hair, with dyeing compositions containing direct dyes. Direct dyes are dye molecules having affinity for keratinous fibers. The dyeing method which uses them is a so-called direct dyeing method which comprises allowing the direct dyes to act on the fibers, and subsequently rinsing the fibers.

The colors resulting therefrom are temporary or semi-permanent colors, because the nature of the interactions which links the direct dyes to the keratinous fiber, and their desorption from the surface and/or the core of the fiber are responsible for their weak dyeing power, and their poor resistance to washings and perspiration.

Cationic aminoanthraquinones have already been described among the known direct dyes. Such aminoanthraquinones are described in, for example, French Patent Nos. 1,422,016 (and its addition 87,902), 1,391,675, 1,401, 163, 1,379,649, 1,430,089, 1,584,965, 2,050,397, 2,548,895, U.S. Pat. Nos. 5,169,403, 5,314,505, 5,486,629, 5,520,707, and European Patent Nos. 818,193 and 852,136, and contain only one anthraquinone nucleus.

However, in hair dyeing, direct dyes are being continually sought which exhibit increasingly better characteristics.

It is thus after major research studies carried out on this subject that the inventors have discovered a new class of cationic aminoanthraquinones, the cationic aminodianthraquinones containing at least one cationic group Z, with Z being chosen from quaternized aliphatic chains, aliphatic chains containing at least one quaternized saturated ring, and aliphatic chains containing at least one quaternized unsaturated ring.

This new family of dyes can exhibit the very advantageous characteristic feature of greater solubility in the dyeing media. These new dyes can also generate colors, by direct dyeing, having an intensity and a resistance to various attacks to which the hair may be subjected: light, adverse weather conditions, shampoos, and perspiration, which is substantially improved compared with that of the colors produced with known prior art cationic aminoanthraquinones.

This discovery forms the basis of the present invention.

A subject of the present invention is thus the aminodianthraquinones of formula (I)

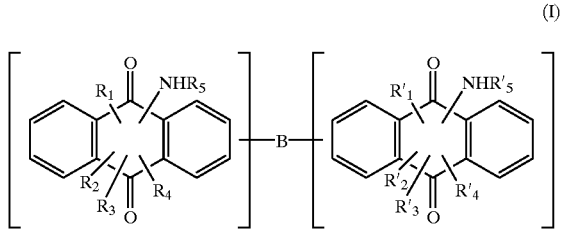

(I)

in which formula,

B is a linking chosen from a linear or branched alkyl chain preferably containing 1 to 14 carbon atoms, which may be interrupted by one or more groups Z, defined below, one or more heteroatoms such as oxygen, sulphur or nitrogen atoms, or a mixture of one or more groups Z and one or more heteroatoms; and which may be unsubstituted or substituted with one or more hydroxyl or $C_1$–$C_6$ alkoxy radicals, and which may carry one or more ketone functions;

$R_1$, $R_2$, $R_3$, $R_4$, $R'_1$, $R'_2$, $R'_3$ and $R'_4$, which may be identical or different, are chosen from one of the two valencies of a linking arm B; a hydrogen atom; a halogen atom; a group Z, defined below; a ($C_1$–$C_6$) alkyl radical; a monohydroxy($C_1$–$C_6$ alkyl) radical; a polyhydroxy($C_2$–$C_6$ alkyl) radical; a cyano radical; a nitro radical; a carboxyl radical; a carbamyl radical; a sulpho radical; a substituted or unsubstituted amino radical, having the same meanings as $NHR_5$ or $NHR'_5$ defined below, and which may be identical or different; a group $OR_6$ or $SR_6$ or $OR'_6$ or $SR'_6$ defined below; $R_5$ and $R'_5$, which may be identical or different, are chosen from one of the two valencies of a linking arm B; a hydrogen atom; a group Z, defined below; a $C_1$–$C_6$ alkyl radical; a monohydroxy($C_1$–$C_6$ alkyl) radical; a polyhydroxy($C_2$–$C_6$ alkyl) radical; a ($C_1$–$C_6$)alkoxy ($C_1$–$C_6$ alkyl) radical; an aryl radical; a benzyl radical; a cyano($C_1$–$C_6$ alkyl) radical; a carbamyl($C_1$–$C_6$ alkyl) radical; an N-($C_1$–$C_6$)alkylcarbamyl($C_1$–$C_6$ alkyl) radical; an N,N-di($C_1$–$C_6$)alkylcarbamyl($C_1$–$C_6$ alkyl) radical; a thiocarbamyl($C_1$–$C_6$ alkyl) radical; a trifluoro ($C_1$–$C_6$ alkyl) radical; a sulpho($C_1$–$C_6$ alkyl) radical; a ($C_1$–$C_6$)alkylcarboxy($C_1$–$C_6$ alkyl) radical; a ($C_1$–$C_6$) alkylsulphinyl($C_1$–$C_6$ alkyl) radical; an aminosulphonyl($C_1$–$C_6$ alkyl) radical; an N-Z-aminosulphonyl($C_1$–$C_6$ alkyl) radical; an N-($C_1$–$C_6$) alkylaminosulphonyl($C_1$–$C_6$ alkyl) radical; an N,N-di ($C_1$–$C_6$)alkylaminosulphonyl($C_1$–$C_6$ alkyl) radical; a ($C_1$–$C_6$)alkylcarbonyl($C_1$–$C_6$ alkyl) radical; an amino ($C_1$–$C_6$ alkyl) radical, wherein the alkyl is unsubstituted or substituted with at least one hydroxyl radical; an amino($C_1$–$C_6$ alkyl) radical, wherein the alkyl is unsubstituted or substituted with at least one hydroxyl radical, and wherein the amine is substituted with at one or two radicals, identical or different, chosen from the $C_1$–$C_6$ alkyl, monohydroxy($C_1$–$C_6$ alkyl), polyhydroxy($C_2$–$C_6$ alkyl), ($C_1$–$C_6$)alkylcarbonyl, carbamyl, N-($C_1$–$C_6$)alkylcarbamyl or N, N-di($C_1$–$C_6$) alkylcarbamyl, ($C_1$–$C_6$)alkylsulphonyl, formyl, trifluoro($C_1$–$C_6$)alkylcarbonyl, ($C_1$–$C_6$)alkylcarboxyl, and thiocarbamyl radicals, or from the group Z, defined below, or which may form, together with the nitrogen atom to which they are attached, a 5- or 6-membered ring containing carbon or containing at least one heteroatom;

$R_6$ and $R'_6$, which may be identical or different, are chosen from one of the two valencies of a linking arm B; a hydrogen atom; a $C_1$–$C_6$ alkyl radical; a monohydroxy ($C_1$–$C_6$ alkyl) radical; a polyhydroxy($C_2$–$C_6$ alkyl) radical; a group Z, defined below; a ($C_1$–$C_6$)alkoxy ($C_1$–$C_6$ alkyl) radical;

an aryl radical; a benzyl radical; a carboxy($C_1$–$C_6$ alkyl) radical; a ($C_1$–$C_6$)alkylcarboxy($C_1$–$C_6$ alkyl) radical; a cyano($C_1$–$C_6$ alkyl) radical; a carbamyl($C_1$–$C_6$ alkyl) radical; an N-($C_1$–$C_6$)alkylcarbamyl($C_1$–$C_6$ alkyl) radical; an N,N-di($C_1$–$C_6$)alkylcarbamyl($C_1$–$C_6$ alkyl) radical; a trifluoro($C_1$–$C_6$ alkyl) radical; an aminosulphonyl($C_1$–$C_6$ alkyl) radical; an N-Z-aminosulphonyl($C_1$–$C_6$ alkyl) radical; an N-($C_1$–$C_6$)alkylaminosulphonyl($C_1$–$C_6$ alkyl) radical; an N,N-di($C_1$–$C_6$)alkylaminosulphonyl($C_1$–$C_6$ alkyl) radical; a ($C_1$–$C_6$)alkylsulphinyl($C_1$–$C_6$ alkyl) radical; a ($C_1$–$C_6$) alkylsulphonyl($C_1$–$C_6$ alkyl) radical; a ($C_1$–$C_6$) alkylcarbonyl($C_1$–$C_6$ alkyl) radical; an amino($C_1$–$C_6$ alkyl) radical, wherein the alkyl is unsubstituted or substituted with at least one hydroxyl radical; an amino($C_1$–$C_6$ alkyl) radical, wherein the alkyl is unsubstituted or substituted with at least one hydroxyl radical, and wherein the amine is substituted with one or two radicals, identical or different, chosen from the $C_1$–$C_6$ alkyl, monohydroxy($C_1$–$C_6$ alkyl), polyhydroxy ($C_2$–$C_6$ alkyl), ($C_1$–$C_6$)alkylcarbonyl, formyl, trifluoro ($C_1$–$C_6$)alkylcarbonyl, ($C_1$–$C_6$)alkylcarboxyl, carbamyl, N-($C_1$–$C_6$)alkylcarbamyl, N,N-di($C_1$–$C_6$)alkylcarbamyl, thiocarbamyl, and ($C_1$–$C_6$)alkylsulphonyl radicals, the groups Z, defined below, or which may form, together with the nitrogen atom to which they are attached, a 5- or 6-membered ring containing carbon or containing at least one heteroatom;

Z is chosen from the unsaturated cationic groups of the formulae (11) and (111), and the saturated cationic groups of the formula (IV):

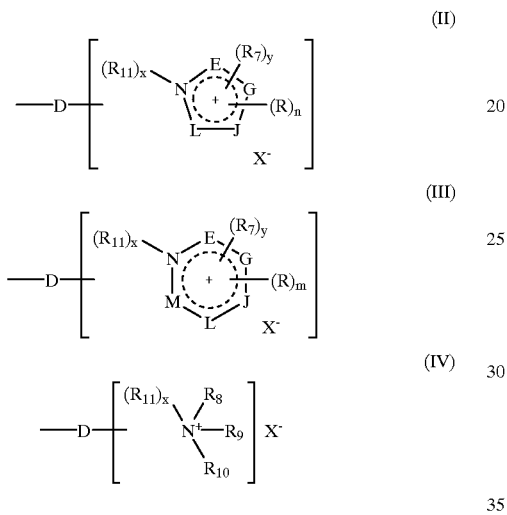

in which:
D is a linking arm chosen from linear and branched alkyl chains, preferably containing from 1 to 14 carbon atoms, which may be interrupted by one or more heteroatoms such as oxygen, sulphur or nitrogen, and which may be substituted with at least one radical chosen from hydroxyl and $C_1$–$C_6$ alkoxy, and which may carry at least one ketone function;

the members E, G, J, L and M, which are identical or different, are chosen from carbon, oxygen, sulphur and nitrogen atoms;

n is an integer ranging from 0 to 4;

m is an integer ranging from 0 to 5;

the radicals R, which are identical or different, are chosen from one of the two valencies of a linking arm B, a second group Z', which has the same definition as the group Z, and which is identical or different from the first group Z; a halogen atom; a hydroxyl radical; a $C_1$–$C_6$ alkyl radical; a monohydroxy($C_1$–$C_6$ alkyl) radical; a polyhydroxy ($C_2$–$C_6$ alkyl) radical; a nitro radical; a cyano radical; a cyano($C_1$–$C_6$ alkyl) radical; a $C_1$–$C_6$ alkoxy radical; a tri($C_1$–$C_6$)alkylsilane($C_1$–$C_6$ alkyl) radical; an amido radical; an aldehydo radical; a carboxyl radical; a $C_1$–$C_6$ alkylcarbonyl radical; a thio radical; a thio($C_1$–$C_6$ alkyl) radical; a ($C_1$–$C_6$) alkylthio radical; an amino radical; an amino radical protected with a ($C_1$–$C_6$)alkylcarbonyl, carbamyl or ($C_1$–$C_6$)alkylsulphonyl radical; a group NHR" or NR"R'", wherein R" and R'", which are identical or different, are chosen from a $C_1$–$C_6$ alkyl radical, a monohydroxy($C_1$–$C_6$ alkyl) radical and a polyhydroxy($C_2$–$C_6$ alkyl) radical;

$R_7$ is chosen from one of the two valencies of a linking arm B; a $C_1$–$C_6$ alkyl radical; a monohydroxy($C_1$–$C_6$ alkyl) radical; a polyhydroxy($C_2$–$C_6$ alkyl) radical; a cyano($C_1$–$C_6$ alkyl) radical; a tri($C_1$–$C_6$)alkylsilane ($C_1$–$C_6$ alkyl) radical; a ($C_1$–$C_6$)alkoxy($C_1$–$C_6$ alkyl) radical; a carbamyl($C_1$–$C_6$ alkyl) radical; a ($C_1$–$C_6$) alkylcarboxy($C_1$–$C_6$ alkyl) radical; a benzyl radical, and a second group Z', which has the same definition as the group Z, which is identical or different from the group Z;

$R_8$, $R_9$ and $R_{10}$, which are identical or different, are chosen from one of the two valencies of a linking arm B; a $C_1$–$C_6$ alkyl radical; a monohydroxy($C_1$–$C_6$ alkyl) radical; a polyhydroxy($C_2$–$C_6$ alkyl) radical; a ($C_1$–$C_6$)alkoxy($C_1$–$C_6$ alkyl) radical; a cyano($C_1$–$C_6$ alkyl) radical; an aryl radical; a benzyl radical; an amido($C_1$–$C_6$ alkyl) radical; a tri($C_1$–$C_6$)alkylsilane ($C_1$–$C_6$ alkyl) radical; an amino($C_1$–$C_6$ alkyl) radical, wherein the amine is protected with a radical chosen from ($C_1$–$C_6$)alkylcarbonyl, carbamyl, and ($C_1$–$C_6$)alkylsulphonyl; two of the radicals $R_8$, $R_9$ and $R_{10}$ may also form, together with the nitrogen atom to which they are attached, a saturated 5- or 6-membered ring containing carbon or capable of containing at least one heteroatom such as, for example, a pyrrolidine ring, a piperidine ring, a piperazine ring or a morpholine ring, it being possible for the ring to be unsubstituted or substituted with a substituent selected from a halogen atom, a hydroxyl radical, a $C_1$–$C_6$ alkyl radical, a monohydroxy($C_1$–$C_6$ alkyl) radical, a polyhydroxy ($C_2$–$C_6$ alkyl) radical, a nitro radical, a cyano radical, a cyano($C_1$–$C_6$ alkyl) radical, a $C_1$–$C_6$ alkoxy radical, a tri($C_1$–$C_6$)alkylsilane($C_1$–$C_6$ alkyl) radical, an amido radical, an aldehydo radical, a carboxyl radical, a keto($C_1$–$C_6$ alkyl) radical, a thio radical, a thio($C_1$–$C_6$ alkyl) radical, a ($C_1$–$C_6$)alkylthio radical, an amino radical, an amino radical protected with a radical chosen from ($C_1$–$C_6$)alkylcarbonyl, carbamyl, and ($C_1$–$C_6$)alkylsulphonyl; one of the radicals $R_8$, $R_9$ and $R_{10}$ may also be chosen from the group Z', having the same definition as the group Z, and which is identical or different from the group Z;

$R_{11}$ is chosen from one of the two valencies of a linking arm B; a $C_1$–$C_6$ alkyl radical; a monohydroxy($C_1$–$C_6$ alkyl) radical; a polyhydroxy($C_2$–$C_6$ alkyl) radical; an aryl radical; a benzyl radical; an amino($C_1$–$C_6$ alkyl) radical, an amino($C_1$–$C_6$ alkyl) radical, wherein the amine is protected with a radical chosen from ($C_1$–$C_6$)alkylcarbonyl, carbamyl, and ($C_1$–$C_6$) alkylsulphonyl; a carboxy($C_1$–$C_6$ alkyl) radical; a cyano($C_1$–$C_6$ alkyl) radical; a carbamyl($C_1$–$C_6$ alkyl) radical; a trifluoro($C_1$–$C_6$ alkyl) radical; a tri($C_1$–$C_6$)alkylsilane($C_1$–$C_6$ alkyl) radical; a sulphonamido($C_1$–$C_6$ alkyl) radical; a ($C_1$–$C_6$) alkylcarboxy($C_1$–$C_6$ alkyl) radical; a ($C_1$–$C_6$) alkylsulphinyl($C_1$–$C_6$ alkyl) radical; a ($C_1$–$C_6$) alkylsulphonyl($C_1$–$C_6$ alkyl) radical; a ($C_1$–$C_6$) alkylketo($C_1$–$C_6$ alkyl) radical; an N-($C_1$–$C_6$) alkylcarbamyl($C_1$–$C_6$ alkyl) radical; an N-($C_1$–$C_6$) alkylsulphonamido($C_1$–$C_6$ alkyl) radical;

x and y are the integers 0 or 1; with the following conditions:

in the unsaturated cationic groups of formula (II):

when x is 0, the linking arm D is attached to the nitrogen atom;

when x is 1, the linking arm D is attached to one of the members E, G, J or L, y is 1:
1) when the members E, G, J and L are simultaneously a carbon atom, and $R_7$ is carried by the nitrogen atom of the unsaturated ring; or
2) when at least one of the members E, G, J and L is a nitrogen atom onto which the radical $R_7$ is attached;

in the unsaturated cationic groups of formula (III):
when x is 0, the linking arm D is attached to the nitrogen atom;
when x is 1, the linking arm D is attached to one of the members E, G, J, L or M;
y is 1 when at least one of the members E, G, J, L and M is a divalent atom, and $R_7$ is carried by the nitrogen atom of the unsaturated ring;

in the cationic groups of formula (IV):
if x is 0, then the linking arm D is attached to the nitrogen atom carrying the radicals $R_8$ to $R_{10}$,
if x is 1, then two of the radicals $R_8$ to $R_{10}$ conjointly form with the nitrogen atom to which they are attached a saturated 5- or 6-membered ring as defined above; and the linking arm D is carried by a carbon atom of the said saturated ring;

$X^-$ is chosen from monovalent and divalent anions; in one embodiment of the invention, X chosen from (i) a halogen atom such as chlorine, bromine, fluorine and iodine, (ii) a hydroxide, (iii) a hydrogen sulphate, and (iv) a $(C_1-C_6)$alkylsulphate such as, for example, methyl sulphate and ethyl sulphate;

it being understood that:
(i) the number of cationic groups Z is at least equal to 1,
(ii) the formula (I) does not designate the compounds of the formula (VI):

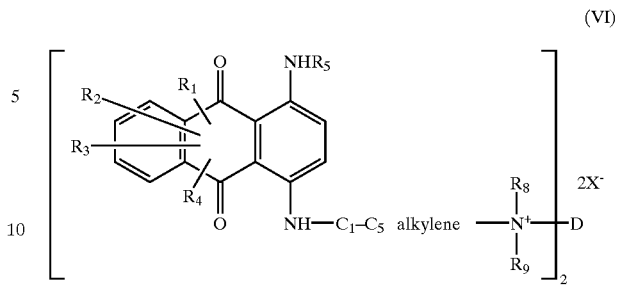

in which
$R_1''$, $R_2''$, $R_3''$ and $R_4''$, which are identical or different, are chosen from a hydrogen atom, a halogen atom, an alkyl radical, and a hydroxyl radical,
$R_5''$ is chosen from a hydrogen atom and an alkyl radical,
$R_8''$ and $R_9''$, which are identical or different, are chosen from an alkyl radical, a mono- or polyhydroxyalkyl radical, and an aryl radical,
D has the same meanings as in formula (I),
$X^-$ designates an anion.

In the above formulae (I), (II), (III) and (IV), the alkyl and alkoxy radicals may be linear or branched.

The compounds of formula (I) may be optionally salified with strong inorganic acids such as HCl, HBr, and $H_2SO_4$, or organic acids such as acetic, tartaric, lactic, citric and succinic acids.

Examples of the rings of the unsaturated groups Z of formula (II), above, include the pyrrole, imidazole, pyrazole, oxazole, thiazole, and triazole rings.

The rings of the unsaturated groups Z of formula (III), above, may be, for example, the pyridine, pyrimidine, pyrazine, oxazine and triazine rings.

In one embodiment of invention, the cationic aminodianthraquinones of formula (I) are chosen from the compounds of the formulae $(I)_2$ to $(I)_{12}$:

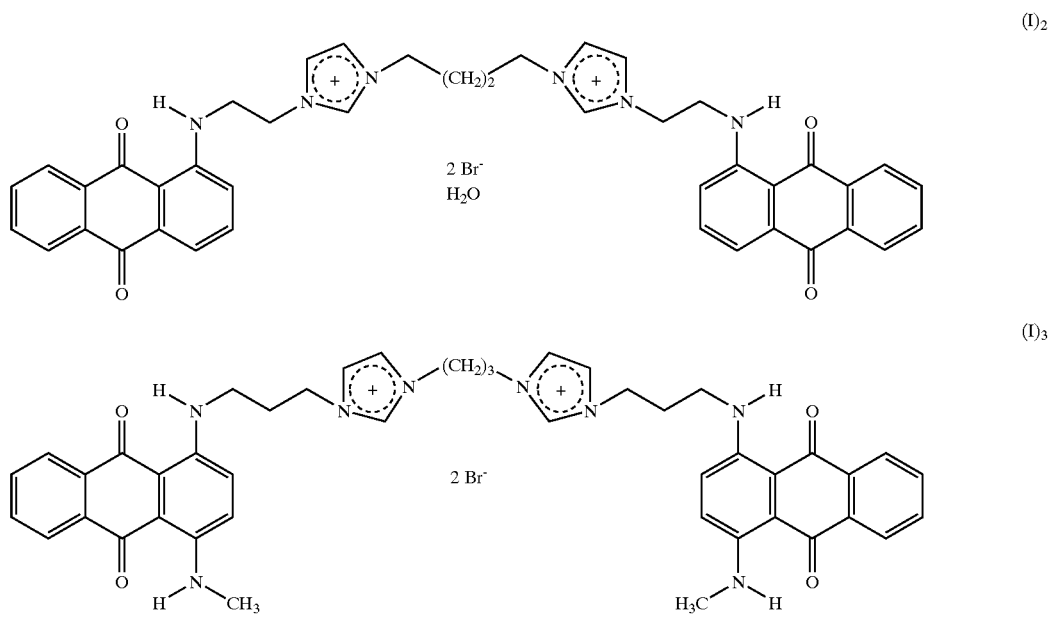

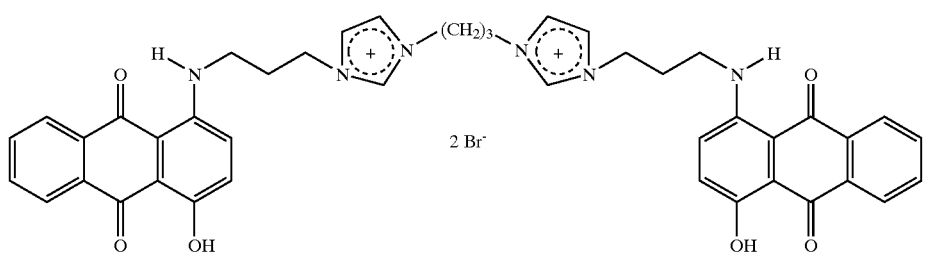
(I)₄
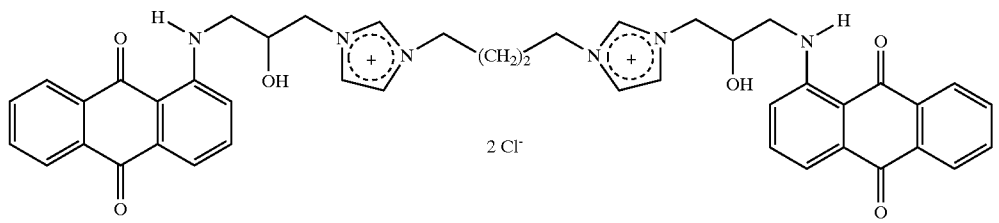
(I)₅
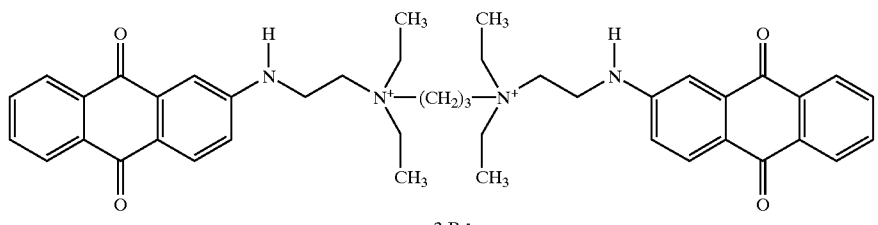
(I)₆
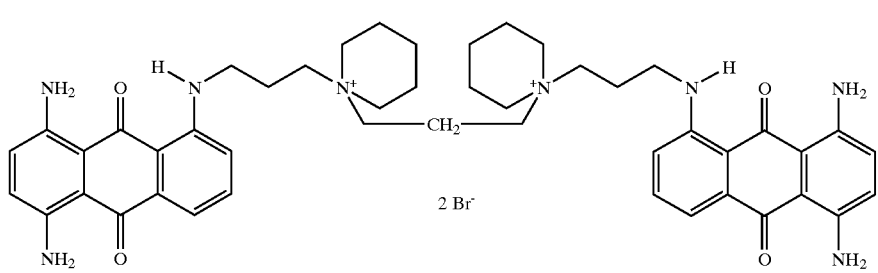
(I)₇
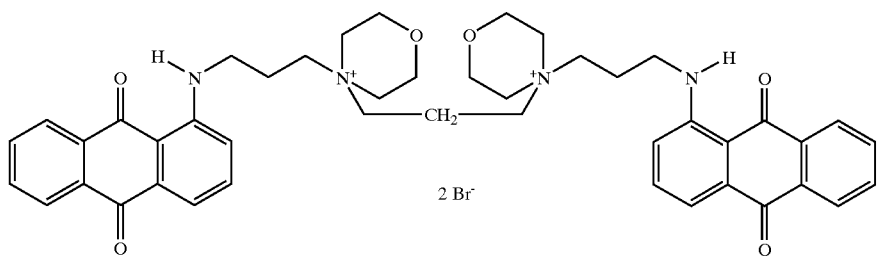
(I)₈
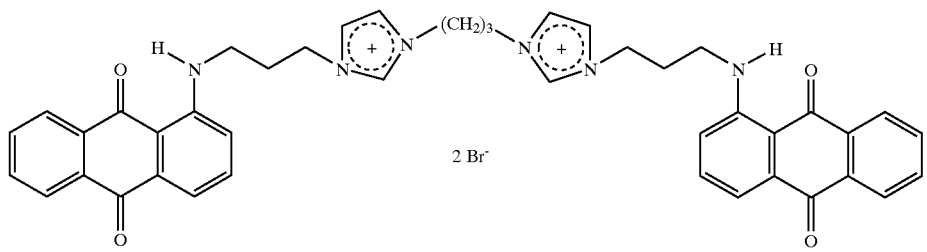
(I)₉

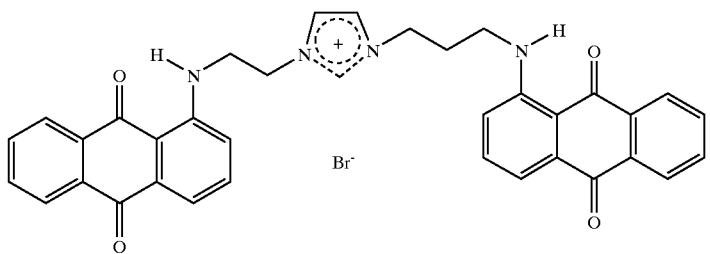

(I)₁₁

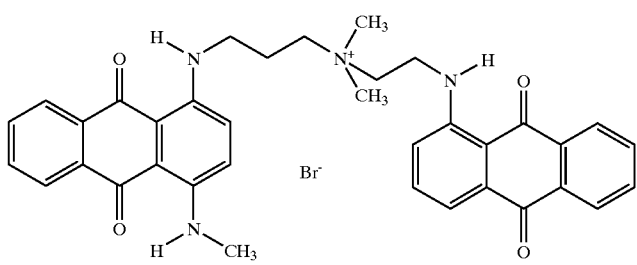

(I)₁₂

The cationic aminodianthraquinones of formula (I) in accordance with the invention can be easily obtained, according to generally well known state of the art methods and in particular, for example, by:

condensation of two anthraquinone molecules containing a haloalkyl radical with a molecule of a compound carrying two tertiary amine radicals separated by a linking arm B as defined in formula (I) described above, or alternatively, condensation of two anthraquinone molecules containing a tertiary amine radical with a molecule of a compound carrying two halogen radicals separated by a linking arm B as defined in formula (I) described above, or alternatively, (a) condensation of an anthraquinone molecule containing a tertiary amine radical with a molecule of a compound carrying two halogen radicals separated by a linking arm B as defined in formula (I) described above, and (b) condensation of a second anthraquinone molecule different from the first and also containing a tertiary amine radical, or alternatively, (a) condensation of an anthraquinone molecule carrying a haloalkyl radical with a molecule of a compound carrying two tertiary amine radicals separated by a linking arm B as defined in formula (I) described above, and (b) condensation of a second anthraquinone molecule different from the first and also carrying a haloalkyl radical, or alternatively, condensation of an anthraquinone molecule containing a tertiary amine radical with an anthraquinone molecule containing a haloalkyl radical.

The quaternization step is generally, for the sake of convenience, the last step in the synthesis, but may occur earlier in the sequence of reactions leading to the preparation of the compounds of formula (I).

A subject of the invention is also dyeing compositions for keratinous materials, comprising, in a medium appropriate for dyeing, an effective quantity for dyeing keratinous materials of at least one cationic $$\left[\begin{array}{c} R_1 \quad O \quad NHR_5 \\ R_2 \\ R_3 \quad R_4 \\ O \end{array}\right] - B - \left[\begin{array}{c} R'_1 \quad O \quad NHR'_5 \\ R'_2 \\ R'_3 \quad R'_4 \\ O \end{array}\right] \quad (I)$$

aminodianthraquinone as defined above by formula (I).

Another subject of the invention is compositions for the direct dyeing of human keratinous fibers such as hair, characterized in that it comprises, in a medium appropriate for dyeing, an effective quantity for dyeing keratinous fibers of at least one cationic aminodianthraquinone as defined above by formula (I).

Another subject of the invention is the use of cationic aminodianthraquinones of formula (I), for which B, $R_1$, $R_2$, $R_3$, $R_4$, $R_5$, $R'_1$, $R'_2$, $R'_3$, $R'_4$ and $R'_5$ have the same meanings as previously described, it being understood that the number of cationic groups Z is at least equal to 1, as direct dyes, in, or for the preparation of, dyeing compositions for keratinous materials, for example human keratinous fibers such as hair.

However other characteristics, aspects and advantages of the invention will emerge even more clearly on reading the description which follows, as well as the various concrete, but not at all limiting, examples intended to illustrate it.

In one embodiment of the dyeing compositions in accordance with the invention, the amount of the at least one cationic aminodianthraquinone(s) of formula (I), or an addition salt thereof, in the dyeing composition ranges from about 0.005 to about 12%, relative to the total weight of the dyeing composition. In another embodiment, the amount of the at least one aminodianthraquinone, or the acid addition salt thereof, ranges from about 0.05 to about 6% by weight, relative to the total weight of the composition.

The cationic aminodianthraquinones of formula (I) in accordance with the invention may also serve, in the well-known oxidation dyeing methods, using oxidation dyes (oxidation dye precursors and optionally couplers), to give the colors obtained with the oxidation dyes different shades or increase their shimmer.

In order to obtain a variety of colors, the dyeing composition according to the invention may also contain, in addition to the cationic aminodianthraquinones of formula (I), at least one additional direct dye that is conventionally used in the art. Examples of the at least on additional direct dye include:

nitrophenylenediamines, nitrodiphenylamines, nitroanilines, nitrophenol ethers, nitrophenols, and nitropyridines; and other anthraquinone dyes different from those in accordance with the present invention; and mono- or diazo, triarylmethane, azine, acridine and xanthene dyes; and metal-containing dyes.

The total amount of all these other direct addition dyes in the composition according to the present invention may range from about 0.5 to about 10% by weight, relative to the total weight of the dyeing composition.

The medium (or carrier) appropriate for dyeing is generally water or a mixture of water and at least one organic solvent for solubilizing the compounds which would not be sufficiently soluble in water. Examples of organic solvents include lower $C_1$–$C_4$ alkanols, such as ethanol and isopropanol; glycerol; glycols and glycol ethers, such as 2-butoxyethanol, propylene glycol, propylene glycol monomethyl ether; as well as aromatic alcohols, such as benzyl alcohol or phenoxyethanol; and similar products and mixtures thereof.

In one embodiment of the invention, the solvents may be present in an amount ranging from approximately 1 to approximately 40% by weight, relative to the total weight of the dyeing composition. In another embodiment of the invention, the amount of solvents may range from approximately 5 to approximately 30% by weight, relative to the total weight of the dyeing composition. It is also possible to add to the composition according to the invention fatty amides such as mono- and diethanolamides of acids derived from copra, lauric acid and oleic acid, in amounts ranging from about 0.05 to about 10% by weight, relative to the total weight of the composition.

It is also possible to add to the composition according to the invention well-known state of the art surfactants of the anionic, cationic, nonionic, amphoteric or zwitterionic type, or mixtures thereof. In one embodiment of the invention, the surfactants can be present in an amount ranging from about 0.1 to about 50% by weight, relative to the total weight of the composition. In another embodiment of the invention, the surfactants can be present in an amount ranging from about 1 to about 20% by weight, relative to the total weight of the composition.

It is also possible to use thickening agents in a proportion ranging from about 0.2 to about 5%.

The dyeing composition according to the invention may contain, in addition, various customary adjuvants such as antioxidants, perfumes, sequestering agents, dispersing agents, hair conditioners, preservatives, and opacifying agents, as well as any other adjuvant normally used in dyeing keratinous materials.

Of course, persons skilled in the art will be careful to choose the optional additional compound(s) mentioned above such that the advantageous properties intrinsically attached to the dyeing composition according to the invention are not, or not substantially, adversely modified by the addition(s) envisaged.

The pH of the dyeing composition in accordance with the invention may vary between approximately 3 and approximately 12. In one embodiment of the invention, the pH varies between approximately 5 and approximately 11. The pH can be adjusted to the desired value by means of acidifying or alkalinizing agents normally used in dyeing keratinous fibres.

Among the acidifying agents, there may be mentioned, by way of example, inorganic or organic acids such as hydrochloric acid, orthophosphoric acid, sulphuric acid, carboxylic acids such as acetic acid, tartaric acid, citric acid, lactic acid, and sulphonic acids.

Suitable alkalinizing agents include ammonium hydroxide, alkali metal carbonates, alkanolamines such as mono-, di- and triethanolamines, as well as their derivatives, sodium and potassium hydroxides, and the compounds of the formula (V):

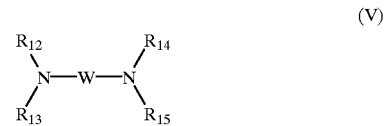

in which W is a propylene residue which is unsubstituted or substituted with a group chosen from a hydroxyl group and a $C_1$–$C_6$ alkyl radical; $R_{12}$, $R_{13}$, $R_{14}$ and $R_{15}$, which are identical or different, are chosen from a hydrogen atom, a $C_1$–$C_6$ alkyl radical, and a hydroxy($C_1$–$C_6$ alkyl) radical.

The dyeing composition according to the invention may be provided in various forms, such as in the form of liquids, creams, gels or in any other form appropriate for dyeing keratinous fibers, and more particularly human keratinous fibers and in particular hair. In particular, it can be packaged under pressure in an aerosol can in the presence of a propellant and can form a foam.

Another subject of the present invention relates to a method for dyeing keratinous fibers, in particular human keratinous fibers such as hair, by direct dyeing, comprising allowing a dyeing composition containing at least one cationic aminodianthraquinone of formula (I) to act on dry or wet keratinous fibers. It is possible to use the composition according to the invention as a leave-in composition, that is to say that after applying the composition to the fibers, they are dried without intermediate rinsing.

In one embodiment, the process comprises allowing the composition to act on the fibers for an exposure time ranging from approximately 3 to approximately 60 minutes, rinsing the fibers, optionally washing the fibers, and rinsing the fibers again and drying the fibers. In another embodiment of the invention, the process is similar to that just described, except that the exposure time ranges from approximately 5 to approximately 45 minutes.

Concrete and nonlimiting examples illustrating the invention will now be given.

EXAMPLES OF PREPARATION

Example 1
Synthesis of the Compound of Formula $(I)_1$

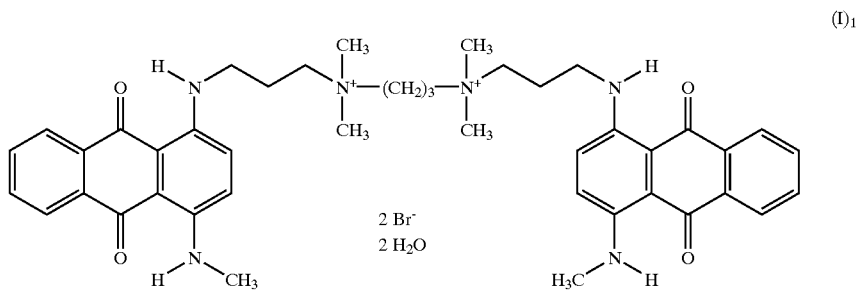

7.0 g (0.0207 mol) of 1-(3-dimethylaminopropylamino)-4-methylaminoanthraquinone (RN-25264-26-0) and 2.09 g (0.1305 mol) of 1,3-dibromopropane (RN-109-64-8) were suspended in 50 ml of 2-methyl-1-propanol. The mixture was then heated, with stirring, at the reflux temperature of the 2-methyl-1-propanol for 4 hours (which corresponds to the disappearance of the starting anthraquinone in thin-layer chromatography); and then the boiling product was dewatered, it was washed with 2-methyl-1-propanol and it was made into a paste again in absolute ethanol.

After drying at 50° C. under vacuum in the presence of phosphoric anhydride, 7.7 g of deep blue crystals were obtained which melt at 214–216° C. (Kofler) and whose elemental analysis calculated for $C_{43}H_{52}N_6O_4Br_2+2H_2O$ was:

| % | C | H | N | O | Br |
|---|---|---|---|---|---|
| theory | 56.58 | 6.18 | 9.21 | 10.52 | 17.51 |
| found | 56.89 | 6.33 | 9.01 | 10.59 | 17.52 |

Example 2
Synthesis of the Compound of Formula $(I)_2$

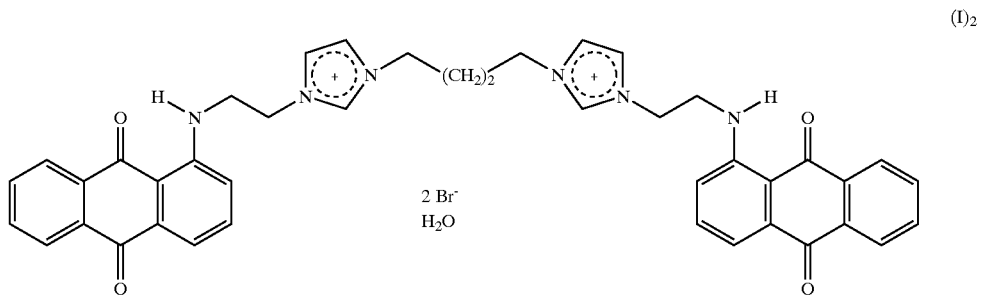

33.0 g (0.1 mol) of 1-(2-bromoethylamino)anthraquinone (RN 3591-05-7) and 10.2 g (0.05 mol) of 1,4-diimidazol-1-ylbutane (RN 69506-86-1) in 180 ml of isobutanol (disappearance of the starting anthraquinone in thin-layer chromatography) were heated under reflux for 7 hours.

The suspension obtained was cooled to room temperature, diluted with 180 ml of absolute ethanol and dewatered.

After purification by recrystallization from 90% ethanol under reflux, drying at 50° C. under vacuum in the presence of phosphoric anhydride, 32.8 g of red crystals melting at 224–225° C. (Kofler) were obtained whose elemental analysis calculated for $C_{42}H_{38}N_6O_4Br_2+H_2O$ was:

| % | C | H | N | O | Br |
|---|---|---|---|---|---|
| theory | 58.08 | 4.64 | 9.68 | 9.21 | 18.40 |
| found | 58.28 | 4.68 | 9.45 | 9.10 | 18.46 |

EXAMPLES OF DYEING COMPOSITIONS

Examples 3 and 4

The two dyeing compositions combined in the following table were prepared:

(all contents expressed in grams—A.M. designates active material)

| | Example 3 | Example 4 |
|---|---|---|
| Dye of formula $(I)_1$ | 0.456 | |
| Dye of formula $(I)_2$ | | 0.434 |

-continued

| | Example 3 | Example 4 |
|---|---|---|
| Hydroxyethylcellulose sold under the name NATROSOL 250 MR by the company Aqualon | 0.72 | 0.72 |
| Benzyl alcohol | 4 | 4 |
| Polyethylene glycol containing 6 ethylene oxide units | 6 | 6 |
| (C8–C10)Alkylpolyglucoside in aqueous solution containing 60% A.M. sold under the name ORAMIX CG 110 by the company Seppic | 4.5 A.M. | 3 A.M. |
| Phosphate buffer pH 7 qs | | 100 |
| Phosphate buffer pH 9 (boric acid/potassium chloride/sodium hydroxide qs | 100 | |

Each of the above compositions was applied to locks of permanently-waved or natural grey hair, which was 90% white, and allowed to act for 20 minutes. After rinsing with running water and drying, the hair was dyed with a shade which is expressed in the table below.

| Composition of Example 3 | Deep blue |
|---|---|
| Composition of Example 4 | Iridescent-copper coloured |

What is claimed is:

1. A direct dyeing composition for human keratinous fibers comprising, in a medium appropriate for dyeing, a quantity of at least one cationic aminodianthraquinone of formula (I), or an acid addition salt thereof, effective for dyeing said human keratinous fibers:

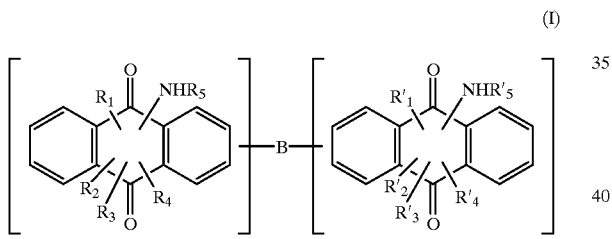

(I)

in which:

B is a linking arm chosen from a linear alkyl chain and a branched alkyl chain, which may be interrupted by one or more groups Z, defined below, one or more heteroatoms, or a mixture of one or more groups Z and one or more heteroatoms, which may be unsubstituted or substituted with at least one hydroxyl or $C_1$–$C_6$ alkoxy radical, and which may carry at least one ketone function;

$R_1$, $R_2$, $R_3$, $R_4$, $R'_1$, $R'_2$, $R'_3$ and $R'_4$, which may be identical or different, are chosen from one of the two valencies of a linking arm B; a hydrogen atom; a halogen atom; a group Z, defined below; a ($C_1$–$C_6$) alkyl radical; a monohydroxy($C_1$–$C_6$ alkyl) radical; a polyhydroxy($C_2$–$C_6$ alkyl) radical; a cyano radical; a nitro radical; a carboxyl radical; a carbamyl radical; a sulpho radical; an unsubstituted amino radical; a substituted amino radical NHR'$_5$, wherein R'$_5$ has the same definition as $R_5$ defined below, and wherein R'$_5$ may be identical to or different from $R_5$ below; and $OR_6$, $SR_6$, $OR'_6$, and $SR'_6$, wherein $R_6$ and $R'_6$ are as defined below;

$R_5$ and $R'_5$, which may be identical or different, are chosen from one of the two valencies of a linking arm B; a hydrogen atom; a group Z, defined below; a $C_1$–$C_6$ alkyl radical; a monohydroxy($C_1$–$C_6$ alkyl) radical; a polyhydroxy($C_2$–$C_6$ alkyl) radical; a ($C_1$–$C_6$)alkoxy ($C_1$–$C_6$ alkyl) radical; an aryl radical; a benzyl radical; a cyano($C_1$–$C_6$ alkyl) radical; a carbamyl($C_1$–$C_6$ alkyl) radical; an N-($C_1$–$C_6$)alkylcarbamyl($C_1$–$C_6$ alkyl) radical; an N,N-di($C_1$–$C_6$)alkylcarbamyl($C_1$–$C_6$ alkyl) radical; a thiocarbamyl($C_1$–$C_6$ alkyl) radical; a trifluoro ($C_1$–$C_6$ alkyl) radical; a sulpho($C_1$–$C_6$ alkyl) radical; a ($C_1$–$C_6$)alkylcarboxy($C_1$–$C_6$ alkyl) radical; a ($C_1$–$C_6$) alkylsulphinyl($C_1$–$C_6$ alkyl) radical; an aminosulphonyl($C_1$–$C_6$ alkyl) radical; an N-Z-aminosulphonyl($C_1$–$C_6$ alkyl) radical; an N-($C_1$–$C_6$) alkylaminosulphonyl($C_1$–$C_6$ alkyl) radical; an N,N-di ($C_1$–$C_6$)alkylaminosulphonyl($C_1$–$C_6$ alkyl) radical; a ($C_1$–$C_6$)alkylcarbonyl($C_1$–$C_6$ alkyl) radical; an amino ($C_1$–$C_6$ alkyl) radical wherein the alkyl is unsubstituted or substituted with at least one hydroxyl radical; an amino($C_1$–$C_6$ alkyl) radical, wherein the alkyl is unsubstituted or substituted with at least one hydroxyl radical, and wherein the amine is substituted with one or two radicals, identical or different, chosen from the $C_1$–$C_6$ alkyl, monohydroxy($C_1$–$C_6$ alkyl), polyhydroxy ($C_2$–$C_6$ alkyl), ($C_1$–$C_6$)alkylcarbonyl, carbamyl, N-($C_1$–$C_6$)alkylcarbamyl, N,N-di($C_1$–$C_6$) alkylcarbamyl, ($C_1$–$C_6$)alkylsulphonyl, formyl, trifluoro($C_1$–$C_6$)alkylcarbonyl, ($C_1$–$C_6$)alkylcarboxyl and thiocarbamyl radicals, or from the group Z, defined below, or which may form, together with the nitrogen atom to which they are attached, a 5- or 6-membered ring containing carbon or containing at least one heteroatom $R_6$ and $R'_6$, which may be identical or different, are chosen from one of the two valencies of a linking arm B; a hydrogen atom; a $C_1$–$C_6$ alkyl radical; a monohydroxy ($C_1$–$C_6$ alkyl) radical; a polyhydroxy($C_2$–$C_6$ alkyl) radical; a group Z, defined below; a ($C_1$–$C_6$)alkoxy ($C_1$–$C_6$ alkyl) radical; an aryl radical; a benzyl radical; a carboxy($C_1$–$C_6$ alkyl) radical; a ($C_1$–$C_6$)alkylcarboxy ($C_1$–$C_6$ alkyl) radical; a cyano($C_1$–$C_6$ alkyl) radical; a carbamyl($C_1$–$C_6$ alkyl) radical; an N-($C_1$–$C_6$) alkylcarbamyl($C_1$–$C_6$ alkyl) radical; an N,N-di($C_1$–$C_6$) alkylcarbamyl($C_1$–$C_6$ alkyl) radical; a trifluoro($C_1$–$C_6$ alkyl) radical; an aminosulphonyl($C_1$–$C_6$ alkyl) radical; an N-Z-aminosulphonyl($C_1$–$C_6$ alkyl) radical; an N-($C_1$–$C_6$)alkylaminosulphonyl($C_1$–$C_6$ alkyl) radical; an N,N-di($C_1$–$C_6$)alkylaminosulphonyl($C_1$–$C_6$ alkyl) radical; a ($C_1$–$C_6$)alkylsulphinyl($C_1$–$C_6$ alkyl) radical; a ($C_1$–$C_6$)alkylsulphonyl($C_1$–$C_6$ alkyl) radical; a ($C_1$–$C_6$)alkylcarbonyl($C_1$–$C_6$ alkyl) radical; an amino ($C_1$–$C_6$ alkyl) radical, wherein the alkyl is unsubstituted or substituted with at least one hydroxyl radical; an amino($C_1$–$C_6$ alkyl) radical, wherein the alkyl is unsubstituted or substituted with at least one hydroxyl radical, and wherein the amine is substituted with one or two radicals, identical or different, chosen from the $C_1$–$C_6$ alkyl, monohydroxy($C_1$–$C_6$ alkyl), polyhydroxy ($C_2$–$C_6$ alkyl), ($C_1$–$C_6$)alkylcarbonyl, formyl, trifluoro ($C_1$–$C_6$)alkylcarbonyl, ($C_1$–$C_6$)alkylcarboxyl, carbamyl, N-($C_1$–$C_6$)alkylcarbamyl, N,N-di($C_1$–$C_6$) alkylcarbamyl, thiocarbamyl and ($C_1$–$C_6$) alkylsulphonyl radicals, or from the groups Z, defined below, or which may form, together with the nitrogen atom to which they are attached, a 5- or 6-membered ring containing carbon or containing at least one heteroatom;

Z is chosen from the unsaturated cationic groups of the formulae (II) and (III), and the saturated cationic groups of the formula (IV)

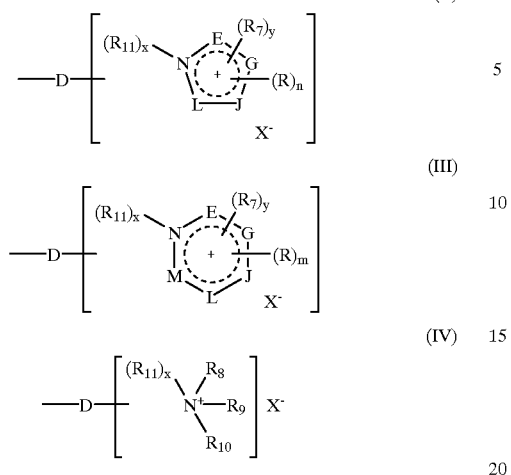

in which
- D is a linking arm chosen from a linear and branched alkyl chain, which may be interrupted by one or more heteroatoms, which may be unsubstituted or substituted with at least one radical chosen from hydroxyl and $C_1$–$C_6$ alkoxy, and which may carry at least one ketone function;
- the members E, G, J, L and M, which are identical or different, are chosen from carbon, oxygen, sulphur or nitrogen atoms;
- n is an integer ranging from 0 to 4;
- m is an integer ranging from 0 to 5;
- the radicals R, which are identical or different, are chosen from one of the two valencies of a linking arm B; a group Z', wherein Z' has the same definition as Z, and wherein the group Z' is identical or different from the group Z; a halogen atom; a hydroxyl radical; a $C_1$–$C_6$ alkyl radical; a monohydroxy($C_1$–$C_6$ alkyl) radical; a polyhydroxy($C_2$–$C_6$ alkyl) radical; a nitro radical; a cyano radical; a cyano($C_1$–$C_6$ alkyl) radical; a $C_1$–$C_6$ alkoxy radical; a tri($C_1$–$C_6$)alkylsilane($C_1$–$C_6$ alkyl) radical; an amido radical; an aldehydo radical; a carboxyl radical; a $C_1$–$C_6$ alkylcarbonyl radical; a thio radical; a thio($C_1$–$C_6$ alkyl) radical; a ($C_1$–$C_6$)alkylthio radical; an amino radical; an amino radical protected with a radical chosen from ($C_1$–$C_6$)alkylcarbonyl, carbamyl and ($C_1$–$C_6$)alkylsulphonyl; and an NHR" or NR"R'" group, wherein R" and R'", which are identical or different, are chosen from a $C_1$–$C_6$ alkyl radical, a monohydroxy($C_1$–$C_6$ alkyl) radical, and a polyhydroxy($C_2$–$C_6$ alkyl) radical;
- $R_7$ is chosen from one of the two valencies of a linking arm B; a $C_1$–$C_6$ alkyl radical; a monohydroxy($C_1$–$C_6$ alkyl) radical; a polyhydroxy($C_2$–$C_6$ alkyl) radical; a cyano($C_1$–$C_6$ alkyl) radical; a tri($C_1$–$C_6$)alkylsilane ($C_1$–$C_6$ alkyl) radical; a ($C_1$–$C_6$)alkoxy($C_1$–$C_6$ alkyl) radical; a carbamyl($C_1$–$C_6$ alkyl) radical; a ($C_1$–$C_6$) alkylcarboxy($C_1$–$C_6$ alkyl) radical; a benzyl radical; a group Z', wherein Z' has the same definition as Z, and wherein the group Z' is identical or different from the group Z;
- $R_8$, $R_9$ and $R_{10}$, which are identical or different, are chosen from one of the two valencies of a linking arm B; a $C_1$–$C_6$ alkyl radical; a monohydroxy($C_1$–$C_6$ alkyl) radical; a polyhydroxy($C_2$–$C_6$ alkyl) a ($C_1$–$C_6$) alkoxy($C_1$–$C_6$ alkyl) radical; a cyano($C_1$–$C_6$ alkyl) radical; an aryl radical; a benzyl radical; an amido ($C_1$–$C_6$ alkyl) radical; a tri($C_1$–$C_6$)alkylsilane($C_1$–$C_6$ alkyl) radical; and an amino($C_1$–$C_6$ alkyl) radical, wherein the amine is protected with a radical chosen from ($C_1$–$C_6$)alkylcarbonyl, carbamyl, and ($C_1$–$C_6$) alkylsulphonyl; two of the radicals $R_8$, $R_9$ and $R_{10}$ may also form, together with the nitrogen atom to which they are attached, a saturated 5- or 6-membered ring containing atoms selected from carbon and heteroatoms, it being possible for the said ring to be unsubstituted or substituted with a halogen atom, a hydroxyl radical, a $C_1$–$C_6$ alkyl radical, a monohydroxy($C_1$–$C_6$ alkyl) radical, a polyhydroxy ($C_2$–$C_6$ alkyl) radical, a nitro radical, a cyano radical, a cyano($C_1$–$C_6$ alkyl) radical, a $C_1$–$C_6$ alkoxy radical, a tri($C_1$–$C_6$)alkylsilane($C_1$–$C_6$ alkyl) radical, an amido radical, an aldehydo radical, a carboxyl radical, a keto($C_1$–$C_6$ alkyl) radical, a thio radical, a thio($C_1$–$C_6$ alkyl) radical, a ($C_1$–$C_6$)alkylthio radical, an amino radical, an amino radical protected with a radical chosen from ($C_1$–$C_6$)alkylcarbonyl, carbamyl and ($C_1$–$C_6$) alkylsulphonyl; one of the radicals $R_8$, $R_9$ and $R_{10}$ may also represent a group Z', wherein Z' has the same definition as Z, and wherein the group Z' is identical or different from the group Z;
- provided that in formula (IV), two of the radicals $R_8$, $R_9$ and $R_{10}$ form a ring chosen from pyrrolidine, piperidine, piperazine, and morpholine, said ring is unsubstituted or substituted with a halogen atom, a hydroxyl radical, a $C_1$–$C_6$ alkyl radical, a monohydroxy($C_1$–$C_6$ alkyl) radical, a polyhydroxy ($C_2$–$C_6$ alkyl) radical, a nitro radical, a cyano radical, a cyano($C_1$–$C_6$ alkyl) radical, a $C_1$–$C_6$ alkoxy radical, a tri($C_1$–$C_6$)alkylsilane($C_1$–$C_6$ alkyl) radical, an amido radical, an aldehydo radical, a carboxyl radical, a ($C_1$–$C_6$ alkyl)carbonyl radical, a thio radical, a thio ($C_1$–$C_6$ alkyl) radical, a ($C_1$–$C_6$)alkylthio radical, an amino radical, and an amino radical protected with a radical chosen from ($C_1$–$C_6$)alkylcarbonyl, carbamyl and ($C_1$–$C_6$)alkylsulphonyl;
- $R_{11}$ is chosen from one of the two valencies of a linking arm B; a $C_1$–$C_6$ alkyl radical; a monohydroxy($C_1$–$C_6$ alkyl) radical; a polyhydroxy($C_2$–$C_6$ alkyl) radical; an aryl radical; a benzyl radical; an amino($C_1$–$C_6$ alkyl) radical; an amino($C_1$–$C_6$ alkyl) radical, wherein the amine is protected with a radical chosen from ($C_1$–$C_6$) alkylcarbonyl, carbamyl, and ($C_1$–$C_6$)alkylsulphonyl; a carboxy($C_1$–$C_6$ alkyl) radical; a cyano($C_1$–$C_6$ alkyl) radical; a carbamyl($C_1$–$C_6$ alkyl) radical; a trifluoro ($C_1$–$C_6$ alkyl) radical; a tri($C_1$–$C_6$)alkylsilane($C_1$–$C_6$ alkyl) radical; a sulphonamido($C_1$–$C_6$ alkyl) radical; a ($C_1$–$C_6$)alkylcarboxy($C_1$–$C_6$ alkyl) radical; a ($C_1$–$C_6$) alkylsulphinyl($C_1$–$C_6$ alkyl) radical; a ($C_1$–$C_6$) alkylsulphonyl($C_1$–$C_6$ alkyl) radical; a ($C_1$–$C_6$) alkylketo($C_1$–$C_6$ alkyl) radical; an N-($C_1$–$C_6$) alkylcarbamyl($C_1$–$C_6$ alkyl) radical; an N-($C_1$–$C_6$) alkylsulphonamido($C_1$–$C_6$ alkyl) radical;
- x and y are integers equal to 0 or 1; with the following conditions:
  - in the unsaturated cationic groups of formula (II):
    - when x is 0, the linking arm D is attached to the nitrogen atom,
    - when x is 1, the linking arm D is attached to one of E, G, J or L,
    - y may only be 1:

1) when the E, G, J and L are simultaneously a carbon atom, and the radical R$_7$ is carried by the nitrogen atom of the unsaturated ring; or
2) when at least one of E, G, J and L represents a nitrogen atom onto which the radical R$_7$ is attached;
in the unsaturated cationic groups of formula (III):
when x is 0, the linking arm D is attached to the nitrogen atom;
when x is 1, the linking arm D is attached to one of E, G, J, L or M,
y may only take the value 1 when at least one of E, G, J, L and M is a divalent atom, and the radical R7 is carried by the nitrogen atom of the unsaturated ring;
in the cationic groups of formula (IV):
when x is 0, then the linking arm D is attached to the nitrogen atom carrying the radicals R8 to R10,
when x is 1, then two of the radicals R$_8$ to R$_{10}$ conjointly form, with the nitrogen atom to which they are attached, a saturated 5- or 6-membered ring as defined above and the linking arm D is carried by a carbon atom of the saturated ring; and
X is chosen from monovalent and divalent anions;
it being understood that:
(i) the number of cat ionic groups Z is at least equal to 1,
(ii) the formula (I) does not designate the compounds of the formula (VI):

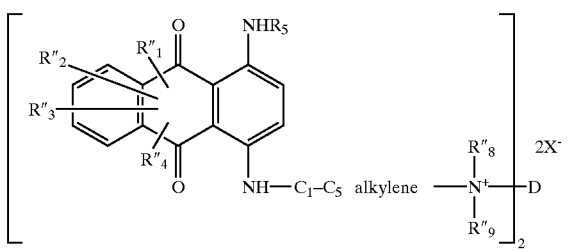

(VI)

in which
R$_1$", R$_2$", R$_3$" and R$_4$", which are identical or different, are chosen from a hydrogen atom, a halogen atom, an alkyl radical and a hydroxyl radical;
R$_5$" is chosen from a hydrogen atom, an alkyl radical, and a monohydroxy(C$_1$–C$_6$ alkyl) radical;
R$_8$" and R$_9$", which are identical or different, are chosen from an alkyl, a mono- or polyhydroxyalkyl radical, and an aryl radical,
D has the same meanings as in formula (I),
X$^-$ is an anion.

2. A composition according to claim 1, wherein said composition has a pH ranging from about 3 to about 12.

3. A composition according to claim 1, wherein said at least one cationic aminodianthraquinone of formula (I) is present in said composition in an amount ranging from about 0.005 to about 12% by weight relative to the total weight of the composition.

4. A composition according to claim 3, wherein the said at least one cationic aminodianthraquinone of formula (I) is present in an amount ranging from about 0.05 to about 6% by weight relative to the total weight of the composition.

5. A composition according to claim 1, wherein said composition further comprises at least one additional direct dye chosen from nitrobenzene dyes, anthraquinone dyes different from those of formula (I), mono- and diazo dyes, triarylmethane dyes, azine dyes, acridine dyes, xanthene dyes, and metal-containing dyes.

6. A composition according to claim 1, wherein the medium appropriate for dyeing is an aqueous medium chosen from water and a mixture of water and organic solvents chosen from alcohols, glycols and glycol ethers, wherein said medium is present in said composition in an amount ranging from about 1% to about 40% by weight relative to the total weight of the composition.

7. A composition according to claim 6, wherein said medium is present in an amount ranging from about 5% to about 30% by weight relative to the total weight of the composition.

8. A method of direct dyeing keratinous fibers, said method comprising:
applying a direct dyeing composition to said fibers, wherein said fibers can be dry or wet, and wherein said direct dyeing composition comprises, in a medium appropriate for dyeing, a quantity of at least one cationic aminodianthraquinone of formula (I), or an acid addition salt thereof, effective for dyeing said keratinous fibers:

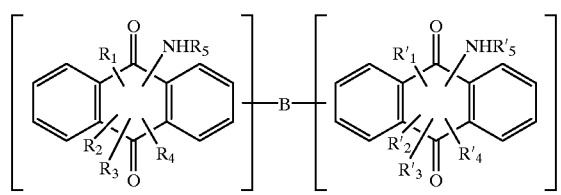

(I)

in which:
B is a linking arm chosen from a linear alkyl chain and a branched alkyl chain, which may be interrupted by one or more groups Z, defined below, one or more heteroatoms, or a mixture of one or more groups Z and one or more heteroatoms, which may be unsubstituted or substituted with at least one hydroxyl or C$_1$–C$_6$ alkoxy radical, and which may carry at least one ketone function;
R$_1$, R$_2$, R$_3$, R$_4$, R'$_1$, R'$_2$, R'$_3$ and R'$_4$, which may be identical or different, are chosen from one of the two valencies of a linking arm B; a hydrogen atom; a halogen am; a group Z, defined below; a (C$_1$–C$_6$)alkyl radical; a monohydroxy(C$_1$–C$_6$ alkyl) radical; a polyhydroxy(C$_2$–C$_6$ alkyl) radical; a cyano radical; a nitro radical; a carboxyl radical; a carbamyl radical; a sulpho radical; an unsubstituted amino radical; a substituted amino radical NHR'$_5$, wherein R'$_5$ has the same definition as R$_5$ defined below, and wherein R'$_5$ may be identical to or different from R$_5$ below; and OR$_6$, SR$_6$, OR'$_6$, and SR'$_6$, wherein R$_6$ and R'$_6$ are as defined below;
R$_5$ and R'$_5$, which may be identical or different, are chosen from one of the two valencies of a linking arm B; a hydrogen atom; a group Z defined below; a C$_1$–C$_6$ alkyl radical; a monohydroxy(C$_1$–C$_6$ alkyl) radical; a polyhydroxy(C$_2$–C$_6$ alkyl) radical; a (C$_1$–C$_6$)alkoxy (C$_1$–C$_6$ alkyl) radical; an aryl radical; a benzyl radical; a cyano(C$_1$–C$_6$ alkyl) radical; a carbamyl(C$_1$–C$_6$ alkyl) radical; an N-(C$_1$–C$_6$)alkylcarbamyl(C$_1$–C$_6$ alkyl) radical; an N,N-di(C$_1$–C$_6$)alkylcarbamyl(C$_1$–C$_6$ alkyl) radical; a thiocarbamyl(C$_1$–C$_6$ alkyl) radical; a trifluoro ($C_1$–$C_6$ alkyl) radical; a sulpho($C_1$-$C_6$ alkyl) radical; a ($C_1$–$C_6$)alkylcarboxy($C_1$–$C_6$ alkyl) radical; a ($C_1$–$C_6$) alkylsulphinyl($C_1$–$C_6$ alkyl) radical; an aminosulphonyl($C_1$–$C_6$ alkyl) radical; an N-Z-aminosulphonyl($C_1$–$C_6$ alkyl) radical; an N-($C_1$–$C_6$) alkylaminosulphonyl($C_1$–$C_6$ alkyl) radical; an N,N-di ($C_1$–$C_6$)alkylaminosulphonyl($C_1$–$C_6$ alkyl) radical; a ($C_1$–$C_6$)alkylcarbonyl($C_1$–$C_6$ alkyl) radical; an amino ($C_1$–$C_6$ alkyl) radical wherein the alkyl is unsubstituted or substituted with at least one hydroxyl radical; an amino($C_1$–$C_6$ alkyl) radical, wherein the alkyl is unsubstituted or substituted with at least one hydroxyl radical, and wherein the amine is substituted with one or two radicals, identical or different, chosen from the $C_1$–$C_6$ alkyl, monohydroxy($C_1$–$C_6$ alkyl), polyhydroxy ($C_2$–$C_6$ alkyl), ($C_1$–$C_6$)alkylcarbonyl, carbamyl, N-($C_1$–$C_6$)alkylcarbamyl, N,N-di($C_1$–$C_6$)alkylcarbamyl, ($C_1$–$C_6$)alkylsulphonyl, formyl, trifluoro($C_1$–$C_6$)alkylcarbonyl, ($C_1$–$C_6$)alkylcarboxyl and thiocarbamyl radicals, or from the group Z, defined below, or which may form, together with the nitrogen atom to which they are attached, a 5- or 6-membered ring containing carbon or containing at least one heteroatom;

$R_6$ and $R'_6$, which may be identical or different, are chosen from one of the two valencies of a linking arm B; a hydrogen atom; a $C_1$–$C_6$ alkyl radical; a monohydroxy ($C_1$–$C_6$ alkyl) radical; a polyhydroxy($C_2$–$C_6$ alkyl) radical; a group Z, defined below; a ($C_1$–$C_6$)alkoxy ($C_1$–$C_6$ alkyl) radical; an aryl radical; a benzyl radical; a carboxy($C_1$–$C_6$ alkyl) radical; a ($C_1$–$C_6$)alkylcarboxy ($C_1$–$C_6$ alkyl) radical; a cyano($C_1$–$C_6$ alkyl) radical; a carbamyl($C_1$–$C_6$ alkyl) radical; an N-($C_1$–$C_6$) alkylcarbamyl($C_1$–$C_6$ alkyl) radical; an N,N-di($C_1$–$C_6$) alkylcarbamyl($C_1$–$C_6$ alkyl) radical; a trifluoro($C_1$–$C_6$ alkyl) radical; an aminosulphonyl($C_1$–$C_6$ alkyl) radical; an N-Z-aminosulphonyl($C_1$–$C_6$ alkyl) radical; an N-($C_1$–$C_6$)alkylaminosulphonyl($C_1$–$C_6$ alkyl) radical; an N,N-di($C_1$–$C_6$)alkylaminosulphonyl($C_1$–$C_6$ alkyl) radical; a ($C_1$–$C_6$)alkylsulphinyl($C_1$–$C_6$ alkyl) radical; a ($C_1$–$C_6$)alkylsulphonyl($C_1$–$C_6$ alkyl) radical; a ($C_1$–$C_6$)alkylcarbonyl($C_1$–$C_6$ alkyl) radical; an amino ($C_1$–$C_6$ alkyl) radical, wherein the alkyl is unsubstituted or substituted with at least one hydroxyl radical; an amino($C_1$–$C_6$ alkyl) radical, wherein the alkyl is unsubstituted or substituted with at least one hydroxyl radical, and wherein the amine is substituted with one or two radicals, identical or different, chosen from the $C_1$–$C_6$ alkyl, monohydroxy($C_1$–$C_6$ alkyl), polyhydroxy ($C_2$–$C_6$ alkyl), ($C_1$–$C_6$)alkylcarbonyl, formyl, trifluoro ($C_1$–$C_6$)alkylcarbonyl, ($C_1$–$C_6$)alkylcarboxyl, carbamyl, N-($C_1$–$C_6$)alkylcarbamyl, N, N-di($C_1$–$C_6$) alkylcarbamyl, thiocarbamyl and ($C_1$–$C_6$) alkylsulphonyl radicals, or from the groups Z, defined below, or which may form, together with the nitrogen atom to which they are attached, a 5- or 6-membered ring containing carbon or containing at least one heteroatom;

Z is chosen from the unsaturated cationic groups of the formulae (II) and (III), and the saturated cationic groups of the formula (IV)

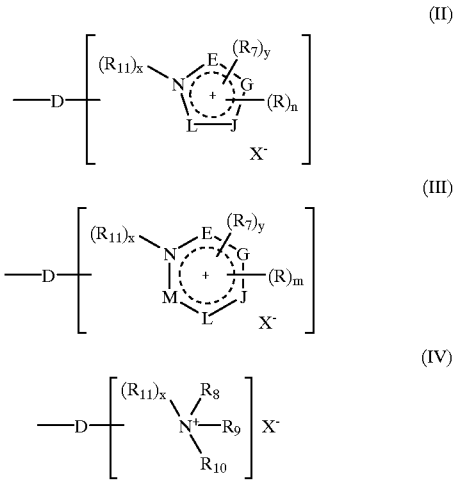

in which
D is a linking arm chosen from a linear and branched alkyl chain, which may be interrupted by one or more heteroatoms, which may be unsubstituted or substituted with at least one radical chosen from hydroxyl and $C_1$–$C_6$ alkoxy, and which may carry at least one ketone function;

the members E, G, J, L and M, which are identical or different, are chosen from carbon, oxygen, sulphur or nitrogen atoms;

n is an integer ranging from 0 to 4;

m is an integer ranging from 0 to 5;

the radicals R, which are identical or different, are chosen from one of the two valencies of a linking arm B; a group Z', wherein Z' has the same definition as Z, and wherein the group Z' is identical or different from the group Z; a halogen atom; a hydroxyl radical; a $C_1$–$C_6$ alkyl radical; a monohydroxy($C_1$–$C_6$ alkyl) radical; a polyhydroxy($C_2$–$C_6$ alkyl) radical; a nitro radical; a cyano radical; a cyano($C_1$–$C_6$ alkyl) radical; a $C_1$–$C_6$ alkoxy radical; a tri($C_1$–$C_6$)alkylsilane($C_1$–$C_6$ alkyl) radical; an amido radical; an aldehydo radical; a carboxyl radical; a $C_1$–$C_6$ alkylcarbonyl radical; a thio radical; a thio($C_1$–$C_6$ alkyl) radical; a ($C_1$–$C_6$)alkylthio radical; an amino radical; an amino radical protected with a radical chosen from ($C_1$–$C_6$)alkylcarbonyl, carbamyl and ($C_1$–$C_6$)alkylsulphonyl; and an NHR" or NR"R"' group, wherein R" and R"', which are identical or different, are chosen from a $C_1$–$C_6$ alkyl radical, a monohydroxy($C_1$–$C_6$ alkyl) radical, and a polyhydroxy ($C_2$–$C_6$ alkyl) radical;

$R_7$ is chosen from one of the two valencies of a linking arm B; a $C_1$–$C_6$ alkyl radical; a monohydroxy($C_1$–$C_6$ alkyl) radical; a polyhydroxy($C_2$–$C_6$ alkyl) radical; a cyano($C_1$–$C_6$ alkyl) radical; a tri($C_1$–$C_6$)alkylsilane ($C_1$–$C_6$ alkyl) radical; a ($C_1$–$C_6$)alkoxy($C_1$–$C_6$ alkyl) radical; a carbamyl($C_1$–$C_6$ alkyl) radical; a ($C_1$–$C_6$) alkylcarboxy($C_1$–$C_6$ alkyl) radical; a benzyl radical; a group Z', wherein Z' has the same definition as Z, and wherein the group Z' is identical or different from the group Z;

$R_8$, $R_9$ and $R_{10}$, which are identical or different, are chosen from one of the two valencies of a linking arm B; a $C_1$–$C_6$ alkyl radical; a monohydroxy($C_1$–$C_6$ alkyl) radical; a polyhydroxy($C_2$–$C_6$ alkyl) radical; a ($C_1$–$C_6$)

alkoxy($C_1$–$C_6$ alkyl) radical; a cyano($C_1$–$C_6$ alkyl) radical; an aryl radical; a benzyl radical; an amido ($C_1$–$C_6$ alkyl) radical; a tri($C_1$–$C_6$)alkylsilane($C_1$–$C_6$ alkyl) radical; and an amino($C_1$–$C_6$ alkyl) radical, wherein the amine is protected with a radical chosen from ($C_1$–$C_6$)alkylcarbonyl, carbamyl, and ($C_1$–$C_6$) alkylsulphonyl; two of the radicals $R_8$, $R_9$ and $R_{10}$ may also form, together with the nitrogen atom to which they are attached, a saturated 5- or 6-membered ring containing atoms selected from carbon and heteroatoms, it being possible for the said ring to be unsubstituted or substituted with a halogen atom, a hydroxyl radical, a $C_1$–$C_6$ alkyl radical, a monohydroxy($C_1$–$C_6$ alkyl) radical, a polyhydroxy ($C_2$–$C_6$ alkyl) radical, a nitro radical, a cyano radical, a cyano($C_1$–$C_6$ alkyl) radical, a $C_1$–$C_6$ alkoxy radical, a tri($C_1$–$C_6$)alkylsilane($C_1$–$C_6$ alkyl) radical, an amido radical, an aldehydo radical, a carboxyl radical, a keto($C_1$–$C_6$ alkyl) radical, a thio radical, a thio($C_1$–$C_6$ alkyl) radical, a ($C_1$–$C_6$)alkylthio radical, an amino radical, an amino radical protected with a radical chosen from ($C_1$–$C_6$)alkylcarbonyl, carbamyl and ($C_1$–$C_6$) alkylsulphonyl; one of the radicals $R_8$, $R_9$ and $R_{10}$ may also represent a group Z', wherein Z' has the same definition as Z, and wherein the group Z' is identical or different from the group Z;

$R_{11}$ is chosen from one of the two valencies of a linking arm B; a $C_1$–$C_6$ alkyl radical; a monohydroxy($C_1$–$C_6$ alkyl) radical; a polyhydroxy($C_2$–$C_6$ alkyl) radical; an aryl radical; a benzyl radical; an amino($C_1$–$C_6$ alkyl) radical; an amino($C_1$–$C_6$ alkyl) radical, wherein the amine is protected with a radical chosen from ($C_1$–$C_6$) alkylcarbonyl, carbamyl, and ($C_1$–$C_6$)alkylsulphonyl; a carboxy($C_1$–$C_6$ alkyl) radical; a cyano($C_1$–$C_6$ alkyl) radical; a carbamyl($C_1$–$C_6$ alkyl) radical; a trifluoro ($C_1$–$C_6$ alkyl) radical; a tri($C_1$–$C_6$)alkylsilane($C_1$–$C_6$ alkyl) radical; a sulphonamido($C_1$–$C_6$ alkyl) radical; a ($C_1$–$C_6$)alkylcarboxy($C_1$–$C_6$ alkyl) radical; a ($C_1$–$C_6$) alkylsulphinyl($C_1$–$C_6$ alkyl) radical; a ($C_1$–$C_6$) alkylsulphonyl($C_1$–$C_6$ alkyl) radical; a ($C_1$–$C_6$) alkylketo($C_1$–$C_6$ alkyl) radical; an N-($C_1$–$C_6$) alkylcarbamyl($C_1$–$C_6$ alkyl) radical; an N-($C_1$–$C_6$) alkylsulphonamido($C_1$–$C_6$ alkyl) radical; x and y are integers equal to 0 or 1; with the following conditions:

in the unsaturated cationic groups of formula (II):
when x is 0, the linking arm D is attached to the nitrogen atom,
when x is 1, the linking arm D is attached to one of E, G, J or L,
y may only be 1:
1) when the E, G, J and L are simultaneously a carbon atom, and the radical $R_7$ is carried by the nitrogen atom of the unsaturated ring; or
2) when at least one of E, G, J and L represents a nitrogen atom onto which the radical $R_7$ is attached;

in the unsaturated cationic groups of formula (III):
when x is 0, the linking arm D is attached to the nitrogen atom;
when x is 1, the linking arm D is attached to one of E, G, J, L or M,
y may only take the value 1 when at least one of E, G, J, L and M is a divalent atom, and the radical $R_7$ is carried by the nitrogen atom of the unsaturated ring;

in the cationic groups of formula (IV):
when x is 0, then the linking arm D is attached to the nitrogen atom carrying the radicals $R_8$ to $R_{10}$, when x is 1, then two of the radicals $R_8$ to $R_{10}$ conjointly form, with the nitrogen atom to which they are attached, a saturated 5- or 6-membered ring as defined above and the linking arm D is carried by a carbon atom of the saturated ring;

X is chosen from monovalent and divalent anions; it being understood that:
(i) the number of cationic groups Z is at least equal to I,
(ii) the formula (I) does not designate the compounds of the formula (VI):

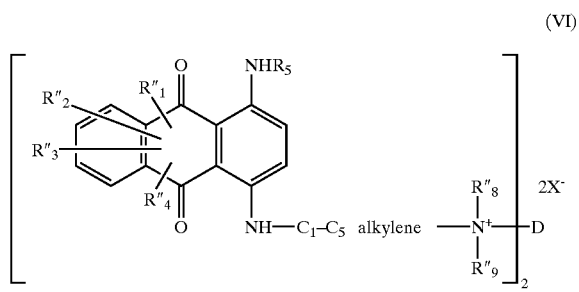

(VI)

in which
$R_1''$, $R_2''$, $R_3''$ and $R_4''$, which are identical or different, are chosen from a hydrogen atom, a halogen atom, an alkyl radical and a hydroxyl radical;
$R_5''$ is chosen from a hydrogen atom, an alkyl radical, and a monohydroxy($C_1$–$C_6$ alkyl) radical;
$R_8''$ and $R_9''$, which are identical or different, are chosen from an alkyl, a mono- or polyhydroxyalkyl radical, and an aryl radical,
D has the same meanings as in formula (I),
$X^-$ is an anion;
and drying said fibers without an intermediate rinsing step.

9. A method of direct dyeing keratinous fibers, said method comprising:
applying a direct dyeing composition to said fibers, wherein said fibers can be wet or dry, and wherein said direct dyeing composition comprises, in a medium appropriate for dyeing, a quantity of at least one cationic aminodianthraquinone of formula (I), or an acid addition salt thereof, effective for dyeing said keratinous fibers:

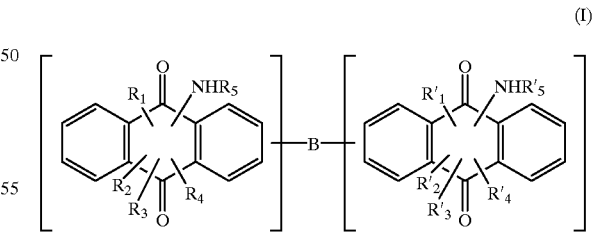

(I)

in which:
B is a linking arm chosen from a linear alkyl chain and a branched alkyl chain, which may be interrupted by one or more groups Z, defined below, one or more heteroatoms, or a mixture of one or more groups Z and one or more heteroatoms, which may be unsubstituted or substituted with at least one hydroxyl or $C_1$–$C_6$ alkoxy radical, and which may carry at least one ketone function;

$R_1$, $R_2$, $R_3$, $R_4$, $R'_1$, $R'_2$, $R'_3$ and $R'_4$, which may be identical or different, are chosen from one of the two valencies of a linking arm B; a hydrogen atom; a halogen atom; a group Z, defined below; a ($C_1$–$C_6$) alkyl radical; a monohydroxy($C_1$–$C_6$ alkyl) radical; a polyhydroxy($C_2$–$C_6$ alkyl) radical; a cyano radical; a nitro radical; a carboxyl radical; a carbamyl radical; a sulpho radical; an unsubstituted amino radical; a substituted amino radical NHR'$_5$, wherein R'$_5$ has the same definition as $R_5$ defined below, and wherein R'$_5$ may be identical to or different from $R_5$ below; and $OR_6$, $SR_6$, $OR'_6$, and $SR'_6$, wherein $R_6$ and $R'_6$ are as defined below;

$R_5$ and $R'_5$, which may be identical or different, are chosen from one of the two valencies of a linking arm B; a hydrogen atom; a group Z, defined below; a $C_1$–$C_6$ alkyl radical; a monohydroxy($C_1$–$C_6$ alkyl) radical; a polyhydroxy($C_2$–$C_6$ alkyl) radical; a ($C_1$–$C_6$)alkoxy ($C_1$–$C_6$ alkyl) radical; an aryl radical; a benzyl radical; a cyano($C_1$–$C_6$ alkyl) radical; a carbamyl($C_1$–$C_6$ alkyl) radical; an N-($C_1$–$C_6$)alkylcarbamyl($C_1$–$C_6$ alkyl) radical; an N,N-di($C_1$–$C_6$)alkylcarbamyl($C_1$–$C_6$ alkyl) radical; a thiocarbamyl($C_1$–$C_6$ alkyl) radical; a trifluoro ($C_1$–$C_6$ alkyl) radical; a sulpho($C_1$–$C_6$ alkyl) radical; a ($C_1$–$C_6$)alkylcarboxy($C_1$–$C_6$ alkyl) radical; a ($C_1$–$C_6$) alkylsulphinyl($C_1$–$C_6$ alkyl) radical; an aminosulphonyl($C_1$–$C_6$ alkyl) radical; an N-Z-aminosulphonyl($C_1$–$C_6$ alkyl) radical; an N-($C_1$–$C_6$) alkylaminosulphonyl($C_1$–$C_6$ alkyl) radical; an N,N-di ($C_1$–$C_6$)alkylaminosulphonyl($C_1$–$C_6$ alkyl) radical; a ($C_1$–$C_6$)alkylcarbonyl($C_1$–$C_6$ alkyl) radical; an amino ($C_1$–$C_6$ alkyl) radical wherein the alkyl is unsubstituted or substituted with at least one hydroxyl radical; an amino($C_1$–$C_6$ alkyl) radical, wherein the alkyl is unsubstituted or substituted with at least one hydroxyl radical, and wherein the amine is substituted with one or two radicals, identical or different, chosen from the $C_1$–$C_6$ alkyl, monohydroxy($C_1$–$C_6$ alkyl), polyhydroxy ($C_2$–$C_6$ alkyl), ($C_1$–$C_6$)alkylcarbonyl, carbamyl, N-($C_1$–$C_6$)alkylcarbamyl, N,N-di($C_1$–$C_6$) alkylcarbamyl, ($C_1$–$C_6$)alkylsulphonyl, formyl, trifluoro($C_1$–$C_6$)alkylcarbonyl, ($C_1$–$C_6$)alkylcarboxyl and thiocarbamyl radicals, or from the group Z, defined below, or which may form, together with the nitrogen atom to which they are attached, a 5- or 6-membered ring containing carbon or containing at least one heteroatom;

$R_6$ and $R'_6$, which may be identical or different, are chosen from one of the two valencies of a linking arm B; a hydrogen atom; a $C_1$–$C_6$ alkyl radical; a monohydroxy ($C_1$–$C_6$ alkyl) radical; a polyhydroxy($C_2$–$C_6$ alkyl) radical; a group Z, defined below; a ($C_1$–$C_6$)alkoxy ($C_1$–$C_6$ alkyl) radical; an aryl radical; a benzyl radical; a carboxy($C_1$–$C_6$ alkyl) radical; a ($C_1$–$C_6$)alkylcarboxy ($C_1$–$C_6$ alkyl) radical; a cyano($C_1$–$C_6$ alkyl) radical; a carbamyl($C_1$–$C_6$ alkyl) radical; an N-($C_1$–$C_6$) alkylcarbamyl($C_1$–$C_6$ alkyl) radical; an N,N-di($C_1$–$C_6$) alkylcarbamyl($C_1$–$C_6$ alkyl) radical; a trifluoro($C_1$–$C_6$ alkyl) radical; an aminosulphonyl($C_1$–$C_6$ alkyl) radical; an N-Z-aminosulphonyl($C_1$–$C_6$ alkyl) radical; an N-($C_1$–$C_6$)alkylaminosulphonyl($C_1$–$C_6$ alkyl) radical; an N,N-di($C_1$–$C_6$)alkylaminosulphonyl($C_1$–$C_6$ alkyl) radical; a ($C_1$–$C_6$)alkylsulphinyl($C_1$–$C_6$ alkyl) radical; a ($C_1$–$C_6$)alkylsulphonyl($C_1$–$C_6$ alkyl) radical; a ($C_1$–$C_6$)alkylcarbonyl($C_1$–$C_6$ alkyl) radical; an amino ($C_1$–$C_6$ alkyl) radical, wherein the alkyl is unsubstituted or substituted with at least one hydroxyl radical; an amino($C_1$–$C_6$ alkyl) radical, wherein the alkyl is unsubstituted or substituted with at least one hydroxyl radical, and wherein the amine is substituted with one or two radicals, identical or different, chosen from the $C_1$–$C_6$ alkyl, monohydroxy($C_1$–$C_6$ alkyl), polyhydroxy ($C_2$–$C_6$ alkyl), ($C_1$–$C_6$)alkylcarbonyl, formyl, trifluoro ($C_1$–$C_6$)alkylcarbonyl, ($C_1$–$C_6$)alkylcarboxyl, carbamyl, N-($C_1$–$C_6$)alkylcarbamyl, N,N-di($C_1$–$C_6$) alkylcarbamyl, thiocarbamyl and ($C_1$–$C_6$) alkylsulphonyl radicals, or from the groups Z, defined below, or which may form, together with the nitrogen atom to which they are attached, a 5- or 6-membered ring containing carbon or containing at least one heteroatom;

Z is chosen from the unsaturated cationic groups of the formulae (II) and (III), and the saturated cationic groups of the formula (IV)

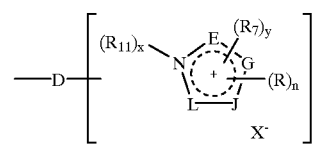
(II)

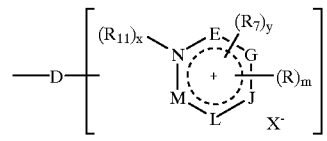
(III)

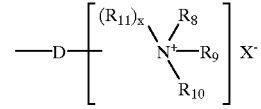
(IV)

in which

D is a linking arm chosen from a linear and branched alkyl chain, which may be interrupted by one or more heteroatoms, which may be unsubstituted or substituted with at least one radical chosen from hydroxyl and $C_1$–$C_6$ alkoxy, and which may carry at least one ketone function;

the members E, G, J, L and M, which are identical or different, are chosen from carbon, oxygen, sulphur or nitrogen atoms;

n is an integer ranging from 0 to 4;

m is an integer ranging from 0 to 5;

the radicals R, which are identical or different, are chosen from one of the two valencies of a linking arm B; a group Z', wherein Z' has the same definition as Z, and wherein the group Z' is identical or different from the group Z; a halogen atom; a hydroxyl radical; a $C_1$–$C_6$ alkyl radical; a monohydroxy($C_1$–$C_6$ alkyl) radical; a polyhydroxy($C_2$–$C_6$ alkyl) radical; a nitro radical; a cyano radical; a cyano($C_1$–$C_6$ alkyl) radical; a $C_1$–$C_6$ alkoxy radical; a tri($C_1$–$C_6$)alkylsilane($C_1$–$C_6$ alkyl) radical; an amido radical; an aldehydo radical; a carboxyl radical; a $C_1$–$C_6$ alkylcarbonyl radical; a thio radical; a thio($C_1$–$C_6$ alkyl) radical; a ($C_1$–$C_6$)alkylthio radical; an amino radical; an amino radical protected with a radical chosen from ($C_1$–$C_6$)alkylcarbonyl, carbamyl and ($C_1$–$C_6$)alkylsulphonyl; and an NHR" or NR"R'" group, wherein R" and R'", which are identical or different, are chosen from a $C_1$–$C_6$ alkyl radical, a monohydroxy($C_1$–$C_6$ alkyl) radical, and a polyhydroxy ($C_2$–$C_6$ alkyl) radical;

$R_7$ is chosen from one of the two valencies of a linking arm B; a $C_1$–$C_6$ alkyl radical; a monohydroxy($C_1$–$C_6$ alkyl) radical; a polyhydroxy($C_2$–$C_6$ alkyl) radical; a cyano($C_1$–$C_6$ alkyl) radical; a tri($C_1$–$C_6$)alkylsilane ($C_1$–$C_6$ alkyl) radical; a ($C_1$–$C_6$)alkoxy($C_1$–$C_6$ alkyl) radical; a carbamyl($C_1$–$C_6$ alkyl) radical; a ($C_1$–$C_6$) alkylcarboxy($C_1$–$C_6$ alkyl) radical; a benzyl radical; a group Z', wherein Z' has the same definition as Z, and wherein the group Z is identical or different from the group Z;

$R_8$, $R_9$ and $R_{10}$, which are identical or different, are chosen from one of the two valencies of a linking arm B; a $C_1$–$C_6$ alkyl radical; a monohydroxy($C_1$–$C_6$ alkyl) radical; a polyhydroxy($C_2$–$C_6$ alkyl) radical; a ($C_1$–$C_6$) alkoxy($C_1$–$C_6$ alkyl) radical; a cyano($C_1$–$C_6$ alkyl) radical; an aryl radical; a benzyl radical; an amido ($C_1$–$C_6$ alkyl) radical; a tri($C_1$–$C_6$)alkylsilane($C_1$–$C_6$ alkyl) radical; and an amino($C_1$–$C_6$ alkyl) radical, wherein the amine is protected with a radical chosen from ($C_1$–$C_6$)alkylcarbonyl, carbamyl, and ($C_1$–$C_6$) alkylsulphonyl; two of the radicals $R_8$, $R_9$ and $R_{10}$ may also form, together with the nitrogen atom to which they are attached, a saturated 5- or 6-membered ring containing atoms selected from carbon and heteroatoms, it being possible for the said ring to be unsubstituted or substituted with a halogen atom, a hydroxyl radical, a $C_1$–$C_6$ alkyl radical, a monohydroxy($C_1$–$C_6$ alkyl) radical, a polyhydroxy ($C_2$–$C_6$ alkyl) radical, a nitro radical, a cyano radical, a cyano($C_1$–$C_6$ alkyl) radical, a $C_1$–$C_6$ alkoxy radical, a tri($C_1$–$C_6$)alkylsilane($C_1$–$C_6$ alkyl) radical, an amido radical, an aldehydo radical, a carboxyl radical, a keto($C_1$–$C_6$ alkyl) radical, a thio radical, a thio($C_1$–$C_6$ alkyl) radical, a ($C_1$–$C_6$)alkylthio radical, an amino radical, an amino radical protected with a radical chosen from ($C_1$–$C_6$)alkylcarbonyl, carbamyl and ($C_1$–$C_6$) alkylsulphonyl; one of the radicals $R_8$, $R_9$ and $R_{10}$ may also represent a group Z', wherein Z' has the same definition as Z, and wherein the group Z' is identical or different from the group Z;

$R_{11}$ is chosen from one of the two valencies of a linking arm B; a $C_1$–$C_6$ alkyl radical; a monohydroxy($C_1$–$C_6$ alkyl) radical; a polyhydroxy($C_2$–$C_6$ alkyl) radical; an aryl radical; a benzyl radical; an amino($C_1$–$C_6$ alkyl) radical; an amino($C_1$–$C_6$ alkyl) radical, wherein the amine is protected with a radical chosen from ($C_1$–$C_6$) alkylcarbonyl, carbamyl, and ($C_1$–$C_6$)alkylsulphonyl; a carboxy($C_1$–$C_6$ alkyl) radical; a cyano($C_1$–$C_6$ alkyl) radical; a carbamyl($C_1$–$C_6$ alkyl) radical; a trifluoro ($C_1$–$C_6$ alkyl) radical; a tri($C_1$–$C_6$)alkylsilane($C_1$–$C_6$ alkyl) radical; a sulphonamido($C_1$–$C_6$ alkyl) radical; a ($C_1$–$C_6$)alkylcarboxy($C_1$–$C_6$ alkyl) radical; a ($C_1$–$C_6$) alkylsulphinyl($C_1$–$C_6$ alkyl) radical; a ($C_1$–$C_6$) alkylsulphonyl($C_1$–$C_6$ alkyl) radical; a ($C_1$–$C_6$) alkylketo($C_1$–$C_6$ alkyl) radical; an N-($C_1$–$C_6$) alkylcarbamyl($C_1$–$C_6$ alkyl) radical; an N-($C_1$–$C_6$) alkylsulphonamido($C_1$–$C_6$ alkyl) radical;

x and y are integers equal to 0 or 1; with the following conditions:
in the unsaturated cationic groups of formula (II):
when x is 0, the linking arm D is attached to the nitrogen atom,
when x is 1, the linking arm D is attached to one of E, G, J or L, y may only be 1:
1) when the E, G, J and L are simultaneously a carbon atom, and the radical $R_7$ is carried by the nitrogen atom of the unsaturated ring; or
2) when at least one of F, G, J and L represents a nitrogen atom onto which the radical $R_7$ is attached;

in the unsaturated cationic groups of formula (III):
when x is 0, the linking arm D is attached to the nitrogen atom;
when x is 1, the linking arm D is attached to one of E, G, J, L or M,
y may only take the value I when at least one of E, G, J, L and M is a divalent atom, and the radical $R_7$ is carried by the nitrogen atom of the unsaturated ring;

in the cationic groups of formula (IV):
when x is 0, then the linking arm D is attached to the nitrogen atom carrying the radicals $R_8$ to $R_{10}$,
when x is 1, then two of the radicals $R_8$ to $R_{10}$ conjointly form, with the nitrogen atom to which they are attached, a saturated 5- or 6-membered ring as defined above and the linking arm D is carried by a carbon atom of the saturated ring;

X is chosen from monovalent and divalent anions;
it being understood that:
(i) the number of cationic groups Z is at least equal to 1,
(ii) the formula (I) does not designate the compounds of the formula (VI):

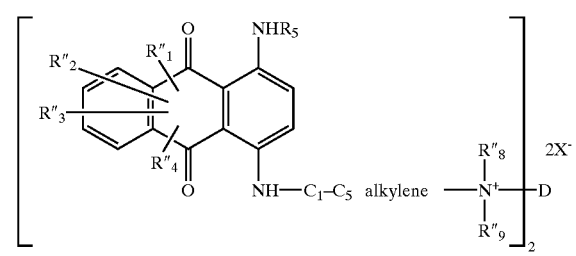

in which $R_1''$, $R_2''$, $R_3''$ and $R_4''$, which are identical or different, are chosen from a hydrogen atom, a halogen atom, an alkyl radical and a hydroxyl radical;

$R_5''$ is chosen from a hydrogen atom, an alkyl radical, and a monohydroxy($C_1$–$C_6$ alkyl) radical;

$R_8''$ and $R_9''$, which are identical or different, are chosen from an alkyl, a mono- or polyhydroxyalkyl radical, and an aryl radical, D has the same meanings as in formula (I), X is an anion;

allowing said direct dyeing composition to remain in contact with said fibers for a time period ranging from approximately 3 to approximately 60 minutes;

rinsing said fibers; and drying said fibers.

10. A method according to claim 9, further comprising, after said rinsing step, a washing step, and an additional rinsing step.

* * * * *

UNITED STATES PATENT AND TRADEMARK OFFICE
CERTIFICATE OF CORRECTION

PATENT NO. : 6,554,872 B2
DATED : April 29, 2003
INVENTOR(S) : Alain Genet et al.

It is certified that error appears in the above-identified patent and that said Letters Patent is hereby corrected as shown below:

Column 16,
Lines 29-30, after "heteroatom", insert a semicolon.
Line 45, "N ,N-di($C_1$-$C_6$)alkylaminosulphonyl($C_1$-$C_6$ alkyl)" should read
-- N,N-di-($C_1$-$C_6$)alkylaminosulphonyl($C_1$-$C_6$ alkyl) --.

Column 17,
Line 50, "wherein R" and R"" should read -- wherein R" and R'" --.

Column 19,
Line 10, "1,the" should read -- 1, the --.
Line 14, "R7" should read -- $R_7$ --.
Line 18, "R8 to R10," should read -- $R_8$ to $R_{10}$, --.
Line 26, "cat ionic" should read -- cationic --.
Between lines 30-40, in the structure for formula (VI)

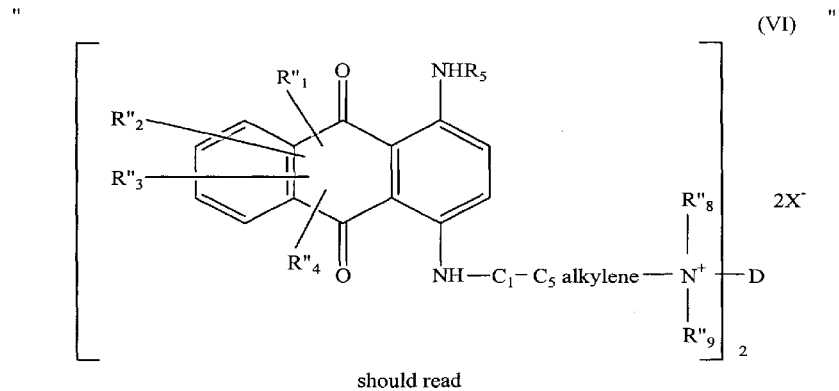

should read

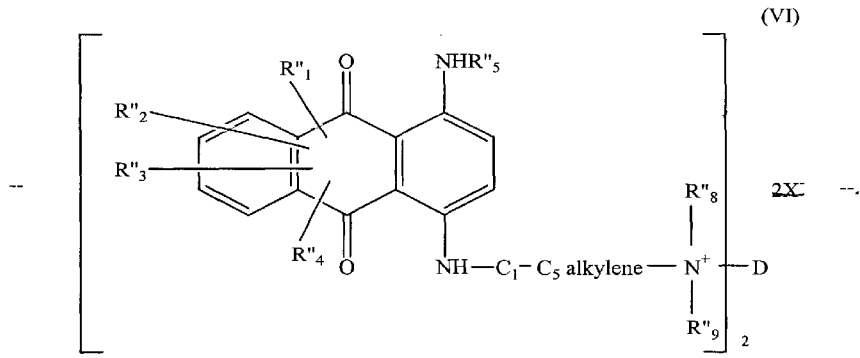

UNITED STATES PATENT AND TRADEMARK OFFICE
CERTIFICATE OF CORRECTION

PATENT NO.    : 6,554,872 B2
DATED         : April 29, 2003
INVENTOR(S)   : Alain Genet et al.

It is certified that error appears in the above-identified patent and that said Letters Patent is hereby corrected as shown below:

Column 20,
Line 48, "halogen am;" should read -- halogen atom; --.
Line 56, "$OR'_6$ ," should read -- $OR'_6$, --.
Line 60, after "group Z", insert a comma.

Column 21,
Line 44, "$(C_1-C_6)$alkylsulphinyl$(C_1-C_6$ alkyl)" should read
-- $(C_1-C_6)$alkylsulphinyl$(C_1-C_6$ alkyl) --.
Lines 57-58, "N, N-di$(C_1-C_6)$alkylcarbamyl," should read
-- N,N-di$(C_1-C_6)$alkylcarbamyl, --.

Column 24,
Line 9, "I," should read -- 1, --.
Between lines 12-23, in the structure for formula (VI)

"
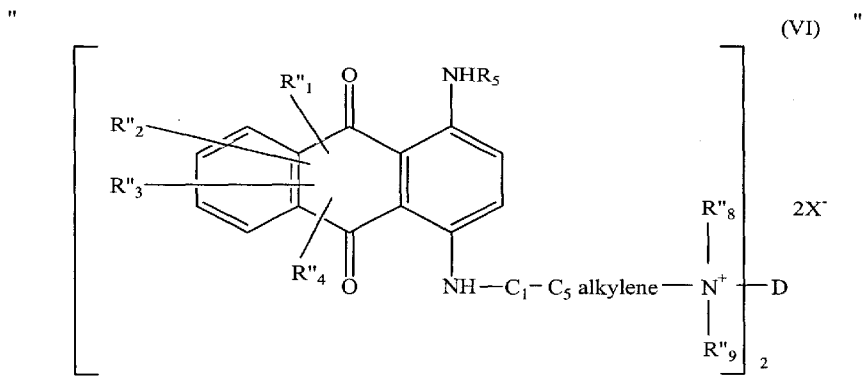
"

should read

--
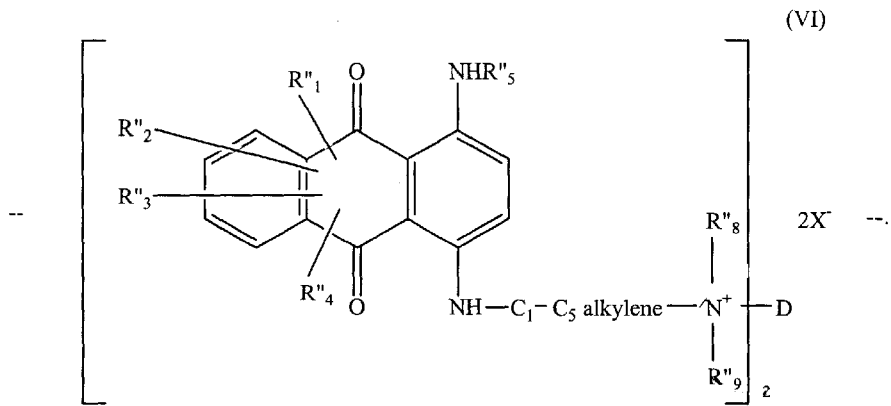
--

UNITED STATES PATENT AND TRADEMARK OFFICE
CERTIFICATE OF CORRECTION

PATENT NO. : 6,554,872 B2
DATED : April 29, 2003
INVENTOR(S) : Alain Genet et al.

It is certified that error appears in the above-identified patent and that said Letters Patent is hereby corrected as shown below:

Column 26,
Lines 8-9, "N, N-di($C_1$-$C_6$)alkylcarbamyl," should read -- N,N-di($C_1$-$C_6$) alkylcarbamyl, --.

Column 27,
Line 12, "group Z" should read -- group Z' --.

Column 28,
Line 5, "one of F," should read -- one of E, --.
Line 13, "value I" should read -- value 1 --.
Between lines 32-43, in the structure for formula (VI)

"
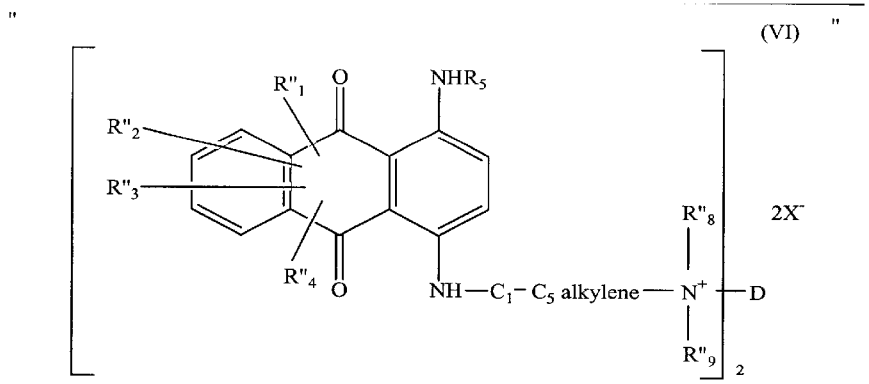

should read

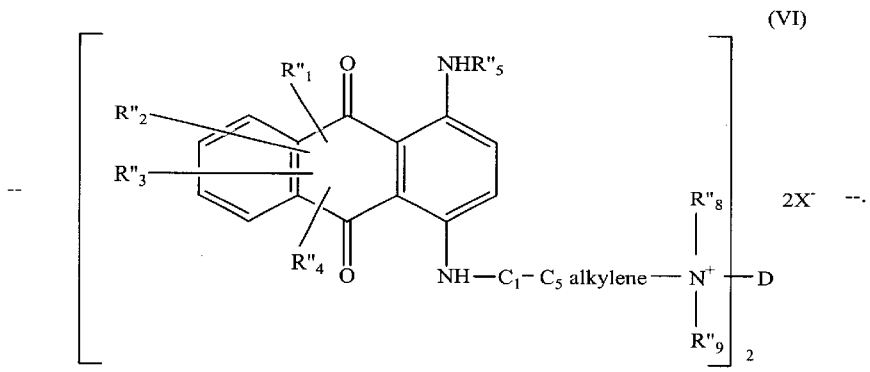
--.

UNITED STATES PATENT AND TRADEMARK OFFICE
CERTIFICATE OF CORRECTION

PATENT NO. : 6,554,872 B2
DATED : April 29, 2003
INVENTOR(S) : Alain Genet et al.

It is certified that error appears in the above-identified patent and that said Letters Patent is hereby corrected as shown below:

<u>Column 28 cont'd,</u>
Line 56, "X is" should read -- X⁻ is --.

Signed and Sealed this

Twenty-sixth Day of August, 2003

JAMES E. ROGAN
*Director of the United States Patent and Trademark Office*